United States Patent [19]

Hodson et al.

[11] 4,012,499

[45] Mar. 15, 1977

[54] CYCLIC SULPHUR COMPOUNDS

[75] Inventors: Harold Francis Hodson, Hayes; John Frederick Batchelor, Beckenham, both of England

[73] Assignee: Burroughs Wellcome Co., Raleigh, N.C.

[22] Filed: June 12, 1975

[21] Appl. No.: 586,426

Related U.S. Application Data

[63] Continuation-in-part of Ser. No. 361,523, May 18, 1973, Pat. No. 3,905,989.

[30] Foreign Application Priority Data

May 19, 1972 United Kingdom ............. 23805/72
Sept. 6, 1972 United Kingdom ............. 41429/72
May 4, 1973 United Kingdom ............. 21174/73

[52] U.S. Cl. ................................. 424/46; 424/45; 424/269
[51] Int. Cl.² .................... A61K 9/14; A61K 31/41
[58] Field of Search ....................... 424/269, 45, 46

[56] References Cited

UNITED STATES PATENTS 3,706,768  12/1972  Bays .............................. 260/308 D

*Primary Examiner*—Frederick E. Waddell

[57] ABSTRACT

Certain tricyclic thioxanthone-10,10-dioxide compounds each of which is substituted in the 1-,2-,3- or 4-position by a carboxyl or (5-tetrazolyl) group and each of which is optionally substituted in the 5-,6-,7- or 8-position by a second carboxyl or (5-tetrazolyl) group or a substituent selected from cyano, halogen, nitro, alkyl, alkoxy, acyl, amino, acylamino, thioalkyl, alkylsulphinyl and alkylsulphonyl, as well as salts, and optionally substituted esters and amides of the carboxyl substituted compounds and alkyl derivatives of the tetrazolyl substituted compounds, are useful for the relief or prophylaxis of allergic conditions.

27 Claims, 2 Drawing Figures

CYCLIC SULPHUR COMPOUNDS

This application is a continuation-in-part of U.S. Ser. No. 361,523 filed May 18, 1973, now U.S. Pat. No. 3,905,989.

The invention relates to tricyclic compounds having medicinal properties, the synthesis of the compounds and their adaptation for medicinal use.

It has been found that tricyclic compounds of formula I, as defined hereinbelow, are active in mammals and in in vitro mammalian preparations as inhibitors of allergic reactions associated with reaginic antibodies of the kind responsible for asthma in man, and that this effect is attributable to the suppression of the release of anaphylactic mediators.

In formula I, $Z^1$ is a substituent in the 1-,2-,3-, or 4-position and is carboxy, 5-tetrazolyl, 5-(1-alkyl) tetrazolyl, or 5-(2-alkyl)tetrazolyl in which the alkyl groups have 1 to 6 carbon atoms and are each optionally substituted by a hydroxyl group or a basic or acidic group; $Z^2$ is hydrogen or a substituent in the 5-,6-,7-, or 8-position selected from the values of the group $Z^1$ as defined above or is alkylsulphonyl, alkylsulphinyl, thioalkyl, amino, acylamino, nitro, cyano, halogen preferably chlorine or bromine, acyl, alkyl or alkoxy wherein the "alkyl" moiety of each of the acyl, alkyl, alkoxy, thioalkyl, acylamino, alkylsulphinyl and alkylsulphonyl groups has 1 to 6 carbon atoms; and $Z^3$ is carbonyl; together with salts of said compounds and when at least one of $Z^1$ and $Z^2$ is a carboxyl group, esters and amides of said compounds.

The inhibition activity of the compounds of formula I has been demonstrated (a) in tests using the response of passive cutaneous anaphylaxis (PCA test) in which is measured the skin reaction produced as the result of interaction between specific antigen injected intravenously and cell-fixed reaginic antibody previously injected into the skin of a mammal (see for example Z. Ovary: Fedn. Proc. Am. Soc. exp. Biol. 24, 94 (1965)), (b) by measurement of the amount of histamine released after antigen challenge of peritoneal mast cells from actively sensitised rats (see for example, 1. Acta Pharmacol. et Toxicol. 30, supp. 1 (1971), 2. Thorax, 27/1, 38 (1972)), and (c) by measurement of the histamine released from human chopped lung tissue passively sensitised in vitro with reaginic antibody when challenged with the homologous antigen (Br. Med. J. 3,272 (1968)). The activity of acids of formula I has been demonstrated as described hereinabove using solutions of the anion.

For the sake of convenience, compounds of formula I wherein either of $Z^1$ and $Z^2$ is or both are an alkyl carboxylate group, are hereinafter referred to as 'esters' of formula I. Similarly references to 'amides' of formula I shall be construed as references to compounds of formula I wherein one or both of $Z^1$ and $Z^2$ is an optionally substituted carboxamide, and references to 'salts' of formula I shall mean salts of formula I wherein one or both of $Z^1$ and $Z^2$ is a salt of the acid.

Pharmaceutically acceptable salts of compounds of formula I include ammonium salts, alkali metal salts such as sodium and potassium salts, alkaline earth salts such as magnesium and calcium salts, and salts of organic bases, for example, amine salts derived from mono-,di-, or tri-lower alkyl or lower alkanolamines such as triethanolamine and diethylaminoethylamine and salts with heterocyclic amines such as piperidine, pyridine, piperazine and morpholine. Especially valuable for intravenous and pulmonary administration are water soluble salts, most preferably those having a solubility in water of at least 1 mg/ml.

For the purposes of medicinal administration, the carboxylate salt group may be a salt of any pharmaceutically acceptable cation, since the pharmacological activity of the salts is associated with the anion.

Suitable amides include amides derived from primary or secondary, aliphatic amines such as N-alkyl and N,N-dialkyl amines for example diethylamine. Suitable esters include esters derived from alkyl alcohols. The alkyl moieties of the alkyl esters and N-alkyl and N,N-dialkyl carboxamides, preferably each have 1 to 6 carbon atoms, most desirably 1 to 4 carbon atoms.

Each of the alkyl moieties of the esters, alkyltetrazoles and amides is optionally substituted by at least one hydroxy, basic or acidic substituent. Suitable basic substituents include amino groups optionally substituted by one or two alkyl groups and heterocyclic amino groups such as piperidine or morpholine. The esters and amides having basic substituents as well as the amides themselves may be in the form of pharmaceutically acceptable acid addition salts.

Suitable acidic substituents include 5-tetrazolyl groups and carboxyl groups, and their pharmaceutically acceptable salts.

Included within the scope of compounds of formula I are tricyclic compounds of formula III wherein $Z^1$ is a substituent in the 1-,2-,3- or 4-position and is a carboxyl group, a carboxylate salt group, an alkyl carboxylate group wherein the alkyl moiety has 1 to 6, preferably 1 to 4 carbon atoms, a carboxamide group optionally N-substituted by alkyl having 1 to 6, preferably 1 to 4 carbon atoms, a 5-tetrazolyl group, a 5-tetrazolyl salt group, a 5-(1-alkyl)tetrazolyl group or a 5-(2-alkyl)tetrazolyl group in which the alkyl groups have 1 to 6 carbon atoms and are each optionally substituted by a basic group;

$Z^2$ is hydrogen or a substituent in the 5-,6-,7-, or 8-position and has the same values as the group $Z^1$ as defined above or is an alkylsulphonyl group, an alkylsulphenyl group, a thioalkyl group, an amino group, an acylamino group, a nitro group, a cyano group, a halogen atom, an acyl group, an alkyl group or an alkoxy group wherein the "alkyl" moiety of each of the acyl, alkyl, alkoxy, thioalkyl, acylamino, alkylsulphinyl and alkylsulphonyl groups has 1 to 6 carbon atoms; and $Z^3$ is carbonyl.

Especially preferred sulphone compounds of formula I include tricyclic compound of formula IV wherein $Z^3$ is as defined in formula I, and $Z^1$ is selected from a carboxyl group, a carboxylate salt group, an alkyl carboxylate group having 1 to 4 carbon atoms in the alkyl moiety, a carboxamide group optionally N-substituted by an alkyl group having 1 to 4 carbon atoms, a 5-tetrazolyl group and a 5-tetrazolyl salt group.

Other preferred compounds of formula I include tricyclic compounds of formula V wherein $Z^3$ is as defined in formula I, and $Z^1$ and $Z^2$ are the same or different and each is selected from a carboxyl group, a carboxylate salt group, an alkyl carboxylate group having 1 to 6 carbon atoms, a carboxamide group optionally N-substituted by an alkyl group having 1 to 6 carbon atoms, a 5-tetrazolyl group, and a 5-tetrazolyl salt group.

Compounds of formula I which show a very high anti-allergic activity on oral administration include 3-carboxythioxanthone-10,10-dioxide and 3-(5-tetrazolyl)thioxanthone-10,10-dioxide, and salts of these compounds, especially alkali metal salts including sodium and potassium salts.

Preferred compounds of the present invention also include tricyclic compounds of formula II wherein $Z^1$ is a substituent in the 3-position and is carboxyl or tetrazolyl and $Z^2$ is hydrogen or a substituent in the 5-,6-,7- or 8-position selected from the values of the group $Z^1$ as defined above or is nitro, chlorine, bromine, or alkyl having 1 to 6 carbon atoms; and the pharmaceutically acceptable salts of said compounds.

Novel thioxanthone-10,10-dioxide compounds of the present invention include tricyclic compounds of formula IX wherein $Z^1$ is a substituent in the 4-,2-,3-, or 4-position and is carboxyl, a carboxylate salt group, an alkyl carboxylate group wherein the alkyl moiety has 1 to 6, preferably 1 to 4 carbon atoms, a 5-tetrazolyl salt group, 5-(1-alkyl)tetrazolyl or 5-(2-alkyl) tetrazolyl in which the alkyl groups have 1 to 6 carbon atoms and are each optionally substituted by a hydroxyl group or a basic or acidic group; and $Z^2$ is a hydrogen or a substituent in the 5-,6-,7-, or 8-position and is alkylsulphonyl, alkylsulphinyl, thioalkyl, amino, acylamino, nitro, cyano, halogen preferably chlorine or bromine, acyl, alkyl, alkoxy wherein the "alkyl" moiety of each of the acyl, alkyl, alkoxy, thioalkyl, acylamino, alkylsulphinyl and alkylsulphonyl groups has 1 to 6 carbon atoms; together with salts of said compounds and when at least one of $Z^1$ and $Z^2$ is a carboxyl group, their esters and amides other than 2-carboxythioxanthone-10,10-dioxide and its methyl ester; 3-carboxy-thioxanthone-10,10-dioxide; 7-nitro-2-carboxythioxanthone-10,10-dioxide and its amide; 2,6-dicarboxythioxanthone-10,10-dioxide and its dimethyl ester: and 8-chloro-2-carboxythioxanthone-10,10-dioxide.

Novel tetrazolyl compounds and their derivatives of the present invention include tricyclic compounds of formula XI wherein $Z^1$ is a substituent in the 1-,2-,3-, or 4-position and is 5-tetrazolyl, a 5-tetrazolyl salt group, 5-(1-alkyl) tetrazolyl or 5-(2-alkyl)tetrazolyl in which the alkyl groups have 1 to 6 carbon atoms and are each optionally substituted by a hydroxyl group or a basic or acidic group; $Z^2$ is a hydrogen or a substituent in the 5-,6-,7-, or 8-position selected from the values of the group $Z^1$ as defined above or is alkylsulphonyl, alkylsulphinyl, thioalkyl, amino, acylamino, nitro, cyano, halogen preferably chlorine or bromine, acyl, alkyl, or alkoxy wherein the "alkyl" moiety of each of the acyl, alkyl, alkoxy, thioalkyl, acylamino, alkylsulphinyl and alkylsulphonyl groups has 1 to 6 carbon atoms, carboxyl, a carboxylate salt group, an alkyl carboxylate group wherein the alkyl moiety has 1 to 6, preferably 1 to 4 carbon atoms, or a carboxamide group optionally N-substituted by alkyl having 1 to 6, preferably 1 to 4 carbon atoms; and $Z^3$ is carbonyl.

Novel compounds of the present invention also include the solid tricyclic compounds of formula XII wherein $Z^1$ is a substituent in the 1-,2-,3-, or 4-position and is a pharmaceutically acceptable carboxylate salt group, 5-tetrazolyl, a 5-tetrazolyl salt group, 5-(1-alkyl)tetrazolyl or 5-(2-alkyl)tetrazolyl in which the alkyl groups have 1 to 6 carbon atoms and are each optionally substituted by a hydroxyl group or a basic or acidic group; $Z^2$ is a hydrogen or a substituent in the 5-,6-,7-, or 8-position selected from the values of the group $Z^1$ defined above or is alkylsulphonyl, alkylsulphinyl, thioalkyl, amino, acylamino, nitro, cyano, halogen preferably chlorine or bromine, acyl, alkyl, or alkoxy wherein the "alkyl" moiety of the acyl, alkoxy, thioalkyl, acylamino, alkylsulphinyl and alkylsulphonyl groups has 1 to 6 carbon atoms or a carboxyl; and $Z^3$ is carbonyl; and when $Z^2$ includes a carboxyl group, esters or amides thereof;

The compounds of formula I may be prepared by known chemical techniques. In general, the methods include cyclisation wherein the central ring is completed by ring closure, hydrolysis, oxidation or reduction of precursors leading to both of the groups $Z^1$ and $Z^2$ by a variety of techniques. Examples of the preparation of certain compounds of formula I by these methods are described at the end of this specification. These general synthetic procedures are also applicable in some instances to the preparation of intermediates.

The cyclisation preparative methods in general include the formation as the final step of one or both of the bridges of the central ring. For example compounds of formula XIII wherein $Z^1,Z^2$ and $Z^3$ are defined in formula (I), may be reacted with chlorosulphonic acid to provide corresponding compounds of formula I, or using chlorosulphonyl compounds of formula XIV wherein $Z^1$, and $Z^2$ and $Z^3$ are defined in formula I, the corresponding compounds of formula I may be prepared, by ring closure using a Lewis acid, for example aluminium chloride with heat.

Reaction of a Lewis acid or a protonic acid with substituted diphenyl sulphones of formula XV wherein $Z^1$ and $Z^2$ are defined in formula I and $R^1$ is a carboxy group or a derivative thereof such as a nitrile, amide, aldehyde, or acid chloride, produces the thioxanthone 10,10-dioxides Preferred protonic acids are polyphosphoric acid (tetraphosphoric acid,) and sulphuric acid. Suitable Lewis acids include aluminium trichloride and boron trifluoride. The reaction is preferably carried out at a temperature from 50° to 300° C.

A variety of oxidation techniques may be used to prepare the compounds of formula (I) by completion of one or both of the bridges of the central ring. For example, thioxanthone-10,10-dioxides (in the formula 1, $Z^3$ is carbonyl) may be prepared by oxidation of the corresponding thioxanthene-10,10-dioxides (in formula I, $Z^3$ is methylene), using for example Triton B, pyridine and oxygen. Compounds of formula I may also be prepared by oxidation of the corresponding sulphoxides and sulphides to form the sulphones, using for example hydrogen peroxide and acetic acid.

The compounds of formula I may also be prepared by formation of one or both of the groups $Z^1$ and $Z^2$ as the final step.

Thus in formula I wherein one or both of $Z^1$ and $Z^2$ are tetrazolyl or (1-alkyl)tetrazolyl groups, these compounds may be prepared by reaction of hydrazoic acid or a salt thereof or nitrous acid with an appropriate compound of formula XVIII wherein $Y^7$ is a group $Z^1$ as defined in formula I or a tetrazolyl group precursor and $Y^8$ is a group $Z^2$ as defined in formula (I) or a tetrazolyl group precursor, provided that at least one of $Y^7$ and $Y^8$ is a tetrazolyl group precursor.

When hydrazoic acid or a salt thereof is used, a suitable tetrazolyl group precursor is a group

wherein $R^3$ and $R^4$ together form a bond (nitrile), $R^3$ is hydrogen or alkyl and $B^4$ is alkoxy having 1 to 6 carbon atoms (imidoester), thioalkyl having 1 to 6 carbon atoms (imidothioester), $-NH-NH_2$ (amidrazone), or amino (amidine) or $R^3$ is hydroxy and $R^4$ is amino (amidoxime), or $R^3$ is alkyl and $R^4$ is halogen (imidohalide). In the case of amidoximes and nitriles, only tetrazolyl compounds may be produced and in the case of imidohalides only alkyltetrazolyl compounds may be produced. The reaction is preferably carried out in a polar aprotic liquid medium using a salt of hydrazoic acid.

When nitrous acid is used a suitable tetrazolyl precursor group is a group

wherein $R^3$ is hydrogen or alkyl and $R^4$ is $-NH-NH_2$ (amidrazone) or $R^3$ is hydrogen and $R^4$ is amino (amidine). In the latter case, reduction of the intermediate nitrosation product, with or without prior isolation, using for example sodium amalgam, is required to give the corresponding tetrazolyl compound.

The tetrazolyl compounds of formula I thus prepared may be isolated as the free acid or as a tetrazolyl salt, and the one converted to the other in known manner and as specifically described below in relation to the carboxylic acids of formula I and their salts.

The 5-(1- and 2-alkyl)tetrazolyl compounds of formula I may be made from the corresponding tetrazolyl compounds of formula I or their salts by akylation.

The carboxylic acids of formula I, wherein one or both of $Z^1$ and $Z^2$ are carbonyl may be prepared by a variety of methods which include as the final step the formation of the carboxyl group. These compounds may be isolated as the free acid, as salts thereof, or converted to amides or esters of formula I, depending upon the nature of the desired products. Thus they may be prepared by hydrolysis of a compound of formula XIX wherein at least one of $Y^1$ and $Y^2$ is a carboxyl group precursor, such as a nitrile group, trichloromethyl group or a group $COL^1$ wherein $L^1$ is a leaving group, such as a nucleophilic atom or group, for example, a trichloromethyl group, an optionally substituted amino group, a halogen atom or an alkoxy group, when the other is $Z^1$ or $Z^2$ as defined in formula I, as appropriate, or is $Y^1$ as defined above; and $Z^3$ has the meaning defined in formula I. Hydrolysis is conveniently effected by heating a compound of formula XIX with a base or a dilute aqueous mineral acid optionally with an organic acid. For example, one may use dilute sulphuric acid or dilute hydrochloric acid with acetic acid.

By means of nucleophilic substitution reactions analogous to hydrolysis, for example, alcoholysis and ammonolysis, esters and amides of formula I may be prepared directly from compounds of formula XIX. Thus reaction of a compound of formula XIX with an appropriate alcohol yields an ester of formula I, and reaction with ammonia or an appropriate primary or secondary amine yields an amide of formula I.

The carboxylic acids of formula I and their salts may also be made by oxidation of a compound of formula XX wherein $Y^5$ is an alkyl group, an acyl group or a group $Z^1$ as defined in formula I, $Z^3$ is as defined in formula I, and Y is an alkyl group, an acyl group or a group $Z^2$ as defined in formula I provided that at least one of $Y^5$ and $Y^6$ is an alkyl or acyl group. Oxidation of compounds wherein $Y^5$ and/or $Y^6$ are lower alkyl groups may be effected with such conventional oxidising agents as acid or alkaline aqueous potassium permanganate solution; chromium trioxide, for example, with acetic acid or sulphuric acid; oxygen in the presence of a conventional catalyst such as vanadium, cobalt and manganese salts or oxides; or aqueous solutions of dichromate salts.

Oxidation of compounds wherein $Y^5$ and/or $Y^6$ are acyl groups may be effected with such conventionl oxidising agents as chromium trioxide, for example, with acetic acid or sulphuric acid; aqueous solutions of salts of hypochlorous and hypobromous acids in the presence of a base; sodium or potassium dichromate with acetic acid; or nitric acid. These oxidation procedures are advantageously effected with heating in the liquid phase.

The compounds of formula I wherein $Z^2$ is other than hydrogen, alkyl, acyl, carboxyl or a derivative thereof or tetrazolyl or a derivative thereof may also be made by formation of the group $Z^2$ as the final step. Such compounds are prepared by introducing an alkylsulphonyl group, alkylsulphinyl group, alkylthio group, amino group, acylamino group, nitro group, cyano group, halogen atom or alkoxy group into an appropriate compound of formula XXII wherein $Z^1$ and $Z^3$ are as defined in formula I and Q is hydrogen, a leaving group or a precursor, by known methods.

Thus where $Z^2$ is amino, the compounds may be made by reduction of the corresponding nitro compounds which themselves may be made by nitration. The amino compounds may be converted into acylamino compounds by acylation and into the corresponding diazonium compounds of formula XXIII wherein $Z^1$ and $Z^3$ are defined in formula I and W is an anion, for example chloride, bromide or hydrogen sulphate by reaction with nitrous acid. These diazonium compounds may be converted by known methods to the alkoxy compounds (by reaction with water and alkylation of the resulting hydroxy compounds); to the halo compounds (by the Sandmeyer reaction using cuprous bromide or chloride; by the Gattermann reaction using a copper catalyst to produce bromo or chloro compound where W is the chloride or bromide ion; by the Balz-Schiemann reaction using the fluoroborate diazonium salt to produce the fluoro compounds; or by using an alkali metal iodide to produce the iodo compounds); to the nitrile compounds (by modified Sandmeyer or Gattermann reactions using cuprous cyanide or potassium cyanide and copper powder); to thiols and alkylthio compounds (by the Leuckart synthesis by formation of diazoxanthates or diazothioxanthates from the diazo compounds and alkali metal alkyl xanthates or thioxanthates respectively which are decomposed in faintly acid cuprous media to the alkylthio compounds and to thiols on hydrolysis). The thiols may if desired be alkylated to the alkylthio compounds of formula I, and these in turn oxidised to alkylsulphinyl or alkylsulphonyl compounds of formula I.

In the operation of the foregoing synthetic methods, it will also be understood that where the groups $Z^1$ and $Z^2$ are formed prior to the complete formation of the desired compound, then in some instances $Z^1$ and/or $Z^2$ must be protected from inter-reaction in the final synthetic stage or stages; thus for example when $Z^2$ is an amino group, it may be protected by acylation and the acylamino group subsequently hydrolysed. In other instances it is advisable to form the groups $Z^1$ and/or $Z^2$ as the final synthetic step, if the group(s) would react in the final synthetic stage(s).

Pharmaceutically acceptable salts of tetrazoles or carboxylic acids of formula I are prepared by any conventional method, for example by neutralising the corresponding carboxylic acid or tetrazole with an appropriate Brönsted base, or by double decomposition of a salt of an acid or tetrazole of formula I so as to produce the desired salt of an appropriate pharmaceutically acceptable cation. The carboxylic acid or tetrazole may be either the isolated acid or tetrazole, or may be present in solution in the reaction mixture resulting from a preparation of the compound, for example by such a method as descried hereinbefore. Suitable Bronsted bases include organic bases such as ethanolamine, and bases containing ammonium, and alkali metal and alkaline earth metal cations. Double decomposition may be effected advantageously in an anion exchange resin wherein a solution of a salt of an acid or tetrazole of formula I is passed through a cation exchange resin, the resin being charged with a pharmaceutically acceptable cation of the suitable base. Double decomposition may also be effected in ordinary solution between a salt of an acid or tetrazole of formula I and a salt of the desired pharmaceutically acceptable cation.

Specifically, pharmaceutically acceptable salts of carboxylic acids of formula I may be prepared by reaction in a polar medium of a compound of formula XXIV wherein $R^7$ and $R^8$ are the same or different and each is selected from a carboxylic group and a group $Y^1$ as defined hereinbefore in formula XIX, and $Z^3$ has the meaning in formula I, with an appropriate Bronsted base and, when the Bronsted base does not contain a hydroxyl ion, in the presence of water. Examples of appropriate Bronsted bases are alkali and alkaline earth metal oxides and hydroxides for producing corresponding alkali and alkaline earth metal salts of formula I. Preferably the reaction is effected with heating.

Salts of formula I may be isolated from a reaction medium by any conventional process for the isolation of salts from a solution thereof in a polar medium. Thus the salts may be isolated by precipitation of the salt or by removal of the polar medium.

Precipitation of the salt may be effected by mixed solvent crystallisation or by the addition of excess of base or salt thereof so as to produce a concentration of the cation of the salt to be isolated, substantially in excess of the molar ratio thereof in said salt to be isolated.

Mixed solvent crystallisation may be effected by addition, to a solution of a salt of formula I in a polar medium, of a second solvent miscible with the solvent already present and in which second solvent the salt of formula I is less soluble than in the solvent already present.

Removal of the polar medium may be effected by evaporation, for example, by freeze-drying, or by azeotropic distillation.

Desirably the salts of formula I are purified prior to incorporation in a pharmaceutical composition. Purification may be effected by any conventional method. A particularly valuable purification process comprises isolation of a crude solid salt of formula I from a reaction mixture wherein said salt has been produced, by any method for the isolation of salts of formula I as described hereinabove; treatment of an aqueous solution of salt with hydrochloric acid; recovery of the corresponding acid of formula I as solid; neutralization of the acid of formula I with Bronsted base of which base the cation is the cation of the required salt of formula I; removal of solid impurities by filtration; and isolation of the salt of formula I by a method as described hereinabove.

Conveniently a carboxylic acid of formula I may be purified prior to neutralization, by recrystallisation or by isolation of a N,N-dimethylformamide adduct and subsequently heating the adduct to drive off the N,N-dimethylformamide. Recrystallisation may be effected using a polar organic solvent optionally containing water, for example, aqueous dimethylformamide, aqueous acetone, or acetic acid may be used.

Esters and amides of acids of formula I may be prepared by any conventional method including esterification of the acid or acid chloride with an alkyl or aryl alcohol to yield the corresponding alkyl or aryl ester respectively and reaction of the acid or acid chloride wwith ammonia or an amine to yield the corresponding amide or substituted amide respectively. Compounds of formula I where $Z^1$ and $Z^2$ are different and are chosen from acid, ester, amide and salt functions, may be prepared by the above methods, and by partial hydrolysis, where appropriate.

The compounds of formula I are useful in the treatment of prophylaxis of mammalian allergic conditions such as asthma and other allergic chest conditions, hay fever (allergic rhinitis), conjunctivitis, urticaria and eczema. In particular they are of value in reaginic mediated Type I hypersensitivity asthma ('extrinsic asthma') and the so-called 'intrinsic asthma' in which no sensitivity to extrinsic antigen can be shown.

The magnitude of a prophylactic or therapeutic dose of compound of formula I will of course vary with the nature and the severity of the allergic condition to be treated and with the particular compound of formula I and its route of administration. In general the dose range lies within the range of 2 $\mu$g. to 100 mg. per Kg. body weight of a mammal.

In the case of an allergic condition as defined hereinbefore, for example, allergic asthma, a suitable dosage is from 5 $\mu$g. to 0.5 mg., preferably form 20 $\mu$g. to 0.2 mg., for example about 0.1 mg., of a compound of formula I, per Kg. of bodyweight of the patient undergoing treatment, when pulmonary administration as described hereinafter is employed. In the case where a composition for intravenous administration is employed a suitable dosage range is from 0.2 to 10 mg. (preferably 1 to 5 mg.) of a compound of formula I per Kg. of bodyweight of patient, and in the case where an oral composition is employed a suitable dosage range is about 30 mg/Kg., e.g. 1 to 50 mg. of a compound of formula I per Kg. of bodyweight of a patient, preferably from 10 to 40 mg/Kg.

In the case where a composition for nasal and ocular administration is employed, for example, in the treatment of allergic rhinitis, a suitable dose is from 0.5 to 25 mg. of a compound of formula I per patient.

The pharmaceutical compositions of the present invention comprise a compound of formula I as an active ingredient, and may also contain pharmaceutically acceptable carrier and optionally other therapeutic ingredients. The compositions include compositions suitable for oral, rectal, opthalmic, pulmonary, nasal, dermal, topical, or parenteral (including subcutaneous, intramuscular and intravenous) administration, although the most suitable route in any given case will depend on the nature and severity of the condition being treated, and on the nature of the active ingredient. They may be conveniently presented in unit dosage form and prepared by any of the methods well known in the art of pharmacy.

Pharmaceutical compositions of the present invention suitable for oral administration may be presented as discrete units such as capsules, cachets or tablets each containing a predetermined amount of the active ingredient; as a powder or granules; or as a solution or a suspension in an aqueous liquid, a non-aqueous liquid, an oil-in-water emulsion or a water-in-oil liquid emulsion. Such compositions may be prepared by any of the methods of pharmacy but all methods include the step of bringing into association the active ingredient with the carrier which constitutes one or more accessory ingredients. In general the compositions are prepared by uniformly and intimately admixing the active ingredient with liquid carriers or finely divided solid carriers or both, and then, if necessary, shaping the product into the desired presentation. For example a tablet may be prepared by compression or moulding, optionally with one or more accessory ingredients. Compressed tablets may be prepared by compressing in a suitable machine, the active ingredient in a free-flowing form such as a powder or granules, optionally mixed with a binder, lubricant, inert diluent, lubricating, surface active or dispersing agent. Moulded tablets may be made by moulding in a suitable machine, a mixture of the powdered compound moistened with an inert liquid diluent. Desirably, each tablet contains from 50mg to 500mg of the active ingredient, and each cachet or capsule contains from 50 to 500mg of the active ingredient.

A particularly valuable form of a pharmaceutical composition of the present invention, for use in the treatment of allergic asthma, is a composition suitable for pulmonary administration via the buccal cavity; although of course conditions other than allergic asthma may also be treated by pulmonary administration of the composition.

Preferably the composition is such that particles having a diameter of 0.5 to $7\mu$ most preferably 1 to $6\mu$, containing active ingredient, are delivered into lungs of a patient. This ensures that a maximal amount of active ingredient is administered to the alveolar sacs of the lungs and retained therein thus producing a maximal effect in the patient. Such compositions are most preferably in the form of dry powders for administration from a powder inhalation device or self-propelling powder-dispensing compositions.

Most preferably the powders of the pulmonary compositions as described hereinabove and hereinbelow comprise particles containing active ingredient of which particles at least 98% by weight have a diameter greater than $0.5\mu$ and at least 95% by number have a diameter less than $7\mu$. Most desirably at least 95% by weight of the particles have a diameter greater than $1\mu$ and at least 90% by number of the particles have a diameter less than $6\mu$.

The compositions in the form of dry powders preferably comprise particles containing the solid active ingredient, the particles having a diameter of 0.5 to $7\mu$ most preferably 1 to $6\mu$. Preferably these compositions include a solid diluent in the form of a fine powder. These compositions may be conveniently presented in a pierceable capsule of a pharmaceutically acceptable material, for example gelatin. Such compositions may be conveniently prepared by comminution of solid active ingredient optionally with a solid diluent. If desired the resulting powder may be filled into a pierceable capsule of a pharmaceutically acceptable material.

Other valuable forms of a composition of the present invention that are suitable for pulmonary administration are self-propelling compositions. These self-propelling compositions may be either powder-dispensing compositions or compositions dispensing the active ingredient in the form of droplets of a solution or suspension.

Self-propelling powder-dispensing compositions preferably comprise dispersed particles of solid active ingredient, having a diameter of 0.5 to $7\mu$ most preferably 1 to $6\mu$ and a liquid propellant having a boiling point of below 65° F at atmospheric pressure. The liquid propellant may be any propellant known to be suitable for medicinal administration and may comprise one or more lower alkyl hydrocarbons, or halogenated lower alkyl hydrocarbons, or mixtures thereof. Chlorinated and fluorinated lower alkyl hydrocarbons are especially preferred as propellant. Generally the propellant may constitute 50 to 99.9% w/w of the composition whilst the active ingredient may constitute 0.1 to 20% w/w, for example, about 2% w/w, of the composition.

The pharmaceutically acceptable carrier in such self-propelling compositions may include other constituents in addition to the propellant, in particular a surfactant or a solid diluent or both. Surfactant are desirable in preventing agglomeration of the particles of active ingredient and in maintaining the active ingredient in suspension. Especially valuable are liquid non-ionic surfactants and solid anionic surfactants or mixtures thereof. Suitable liquid non-ionic surfactants are those having a hydrophile-lipophile balance (HLB, see Journal of the Society of Cosmetic Chemists Vol. 1 pp. 311–326 (1949)) of below 10, in particular esters and partial esters of fatty acids with aliphatic polyhydric alcohols, for instance, sorbitan monooleate and sorbitan trioleate, known commercialy as 'Span 80' (Trade Name) and "Span 85" (Trade Name). The liquid non-ionic surfactant may constitute up to 20% w/w of the composition, though preferably it constitutes below 1% w/w of the composition. Suitable solid anionic surfactants include alkali metal, ammonium and amine salts of dialkyl sulphosuccinate, where the alkyl groups have 4 to 12 carbon atoms, and alkylbenzene sulphonic acid where the alkyl group has 8 to 14 carbon atoms. The solid anionic surfactants may constitute up to 20% w/w of the composition, though preferably below 1% w/w of the composition.

Solid diluents may be advantageously incorporated in such self-propelling compositions where the density of the active ingredient differs substantially from the density of the propellant; also in order to help to maintain the active ingredient in suspension. The solid diluent is in the form of a fine powder, preferably having a particle size of the same order as that of the particles of active ingredients. Suitable solid diluents include sodium chloride and sodium sulphate.

Compositions of the present invention may also be in the form of a self-propelling composition wherein the active ingredient is present in solution. Such self-propelling compositions may comprise an active ingredient, propellant and co-solvent, and advantageously an antioxidant stabiliser. The propellant is one or more of those already cited above. Co-solvents are chosen for their solubility in the propellant, their ability to dissolve the active ingredient, and for their having the lowest boiling point consistent with these above-mentioned properties. Suitable co-solvents are lower alkyl alcohols and ethers and mixtures thereof. The co-solvents may constitute 5 to 40% w/w of the composition, though preferably less than 20% w/w of the composition.

Antioxidant stabilisers may be incorporated in such solution-compositions to inhibit deterioration of the active ingredient and are conveniently alkali metal ascorbates or bisulfites. They are preferably present in an amount of up to 0.25 w/w of the composition.

Such self-propelling compositions may be prepared by any method known in the art. For example the active ingredient either as particles as defined hereinbefore in suspension in a suitable liquid or in up to 20% w/v solution in an acceptable co-solvent as appropriate, is mixed with any other constituents of a pharmaceutically acceptable carrier. The resulting mixture is cooled and introduced into a suitable cooled container and propellant is added thereto in liquid form; and the container is sealed.

Alternatively, such self-propelling compositions may be prepared by mixing the active ingredient either in particles as hereinbefore defined or in 2 to 20% w/v alcohol or aqueous solution as appropriate, together with the remaining constituents of the pharmaceutically acceptable carrier other than propellant; introducing the resulting mixture, optionally with some propellant, into a suitable container; sealing the container; and injecting propellant under pressure into the container at ambient temperature through a valve which comprises a part of the container and is used to control release of the composition from it. Desirably the container is purged by removing air from it at a convenient stage in the preparation of the self-propelling composition.

A suitable container for a self-propelling composition, is one provided with a manually operable valve and being constructed of aluminium, stainless steel or reinforced glass. The valve should of course be one having the desired spray characteristic, that is, the spray issuing from the valve should have the characteristics of particle size as hereinbefore defined. Advantageously the valve is of the metered type, that is a valve of the type which delivers a fixed amount of composition on the occasion of each operation of the valve, for example, about 50 or 100 microliters of composition in each delivery.

Compositions of the present invention may also be in the form of aqueous or dilute alcoholic solution, optionally a sterile solution, of the active ingredient for use in a nebuliser or atomier, wherein an accelerated air stream is used to produce a fine mist consisting of small droplets of the solution. Such compositions usually contain a flavouring agent such as saccharin sodium and a volatile oil. A buffering agent such as sodium phosphate; an antioxidant such as sodium metabisulfite; and a surface active agent may also be included in such a composition. Desirably such a composition should contain a preservative such as methylhydroxybenzoate.

Compositions of the present invention suitable for parenteral administration conveniently comprise sterile aqueous solutions of the active ingredient, which solutions are preferably isotonic with blood of a patient under treatment. These are preferably administered intra-venously, although administration may also be effected by means of subcutaneous or intra-muscular injection. Such compositions may be conveniently prepared by dissolving solid active ingredient in water to produce an aqueous solution, and rendering said solution sterile and isotonic with human blood.

Pharmaceutical compositions of the present invention suitable for topical use include compositions suitable for administration to the skin, eyes, nose and mouth.

Compositions for use on the skin include lotions and creams comprising liquid or semi-solid emulsions, either oil-in-water or water-in-oil, which preferably contain from 0.2 to 5% w/v of the active ingredient. Ointments comprising 0.2 to 5% w/v of the active ingredient dissolved or dispersed in a semi-solid basis may also be used for topical administration to the skin. Conveniently the semi-solid basis contains liquid or semi-solid hydrocarbons, animal fat, wool alcohol or a macrogol, possibly with an emulsifying agent. Desirably the creams and ointments should contain a preservative such as methyl hydroxybenzoate.

Compositions for administration to the eye include eye drops comprising the active ingredient in aqueous or oily solution, preferably at a concentration of 0.2 to 5% w/v. Such solutions are desirably fungistatic and bacteriostatic and are preferably prepared sterile. Compositions for administration to the eye also include eye ointments which preferably comprise the same concentration of active ingredient, conveniently in the form of a salt, either dissolved in one of the ingredients of the semi-solid basis of the ointment or as a finely divided suspension therein.

Compositions suitable for administration to the nose include powder, self-propelling and spray compositions similar to those already described under compositions suitable for pulmonary administration but having when dispersed, a somewhat larger particle size of the order of 10 to 200 microns. In the case of self-propelling solution and spray compositions this effect may be achieved by choice of a valve having the desired spray characteristic i.e. being capable of producing a spray having the desired particle size or by incorporating the medicament as a suspended powder of controlled particle size. Thus the composition instead of passing into the lungs is largely retained in the nasal cavity. Other compositions suitable for nasal administration include a coarse powder having a particle size of 20 to 500 microns which is administered in the manner in which snuff is taken i.e. by rapid inhalation through the nasal passage from a container of the powder held close up to the nose. Another composition suitable for nasal administration is nasal drops comprising 0.2 to 5% w/v of the active ingredient in aqueous or oily solution.

Compositions suitable for topical administration in the mouth include lozenges comprising 10 to 100mg. of the active ingredient in a flavoured basis, usually sucrose and acacia or tragacanth; and pastilles comprising 10 to 100mg. of the active ingredient in an inert basis such as gelatin and glycerin; or sucrose and acacia.

Other therapeutic ingredients suitable for inclusion in the hereinbefore described compositions, especially in the case of those compositions intended for use in the treatment of allergic asthma, include bronchodilators. Any bronchodilator may be used in such a composition although particularly suitable bronchodilators are isoprenaline, adrenaline, orciprenaline, isoethanine and physiologically acceptable acid addition salts thereof, especially isoprenaline sulphate. Conveniently the bronchodilator is present in the composition in an amount of 0.1 to 50% w/w of the weight of active ingredient present.

Included within the scope of the present invention, but in no way limited thereto, are the following specific features:

1. 3-Carboxythioxanthone-10,10-dioxide salts.
2. 3-(5-Tetrazolyl)thioxanthone-10,10-dioxide and salts thereof.
3. A compound of formula I as defined hereinabove, where novel.
4. The synthesis of compounds of formula I as defined hereinabove, by any method known in the art for preparing them and compounds of analogous chemical structure.
5. Pharmaceutical compositions comprising a compound of formula I as defined hereinabove in association with a pharmaceutically acceptable carrier therefor.
6. The preparation of pharmaceutical compositions comprising a compound of formula I as defined hereinabove as an active ingredient, by any conventional method, including admixture of the ingredients.
7. A method of treatment or prophylaxis of mammalian allergic conditions comprising administration of a therapeutic or prophylactic dose respectively, of a compound of formula I as defined hereinabove.
8. Substantially pure solid 3-carboxythioxanthone-10,10-dioxide having a melting point of at least 287° C.

The following preparations and examples illustrate the methods for preparing compounds in accordance with the present invention, as well as compounds and compositions of the present invention. In the examples and preparations, all temperatures are in degrees Celsius. Where melting points are not given for compounds of formula I, the compounds decompose at temperatures below their melting points and/or their melting points are at temperatures above those readily determinable by conventional techniques. In these preparations and examples, the numbering of substituent positions in the tricyclic nucleus used is not necessarily the same as that used in formula I, but is the standard numbering in respect of the particular tricyclic nucleus concerned, as given in the "Ring Index", IInd Edition, Published by The American Chemical Society, 1960. This standard numbering also applies in respect of the individual named compounds disclosed hereinbefore.

REFERENCE PREPARATION 1 - 3-CARBOXYTHIOXANTHONE-10,10-DIOXIDE

A. Preparation of 2,5-dimethyl diphenyl sulphone

Figure 1:
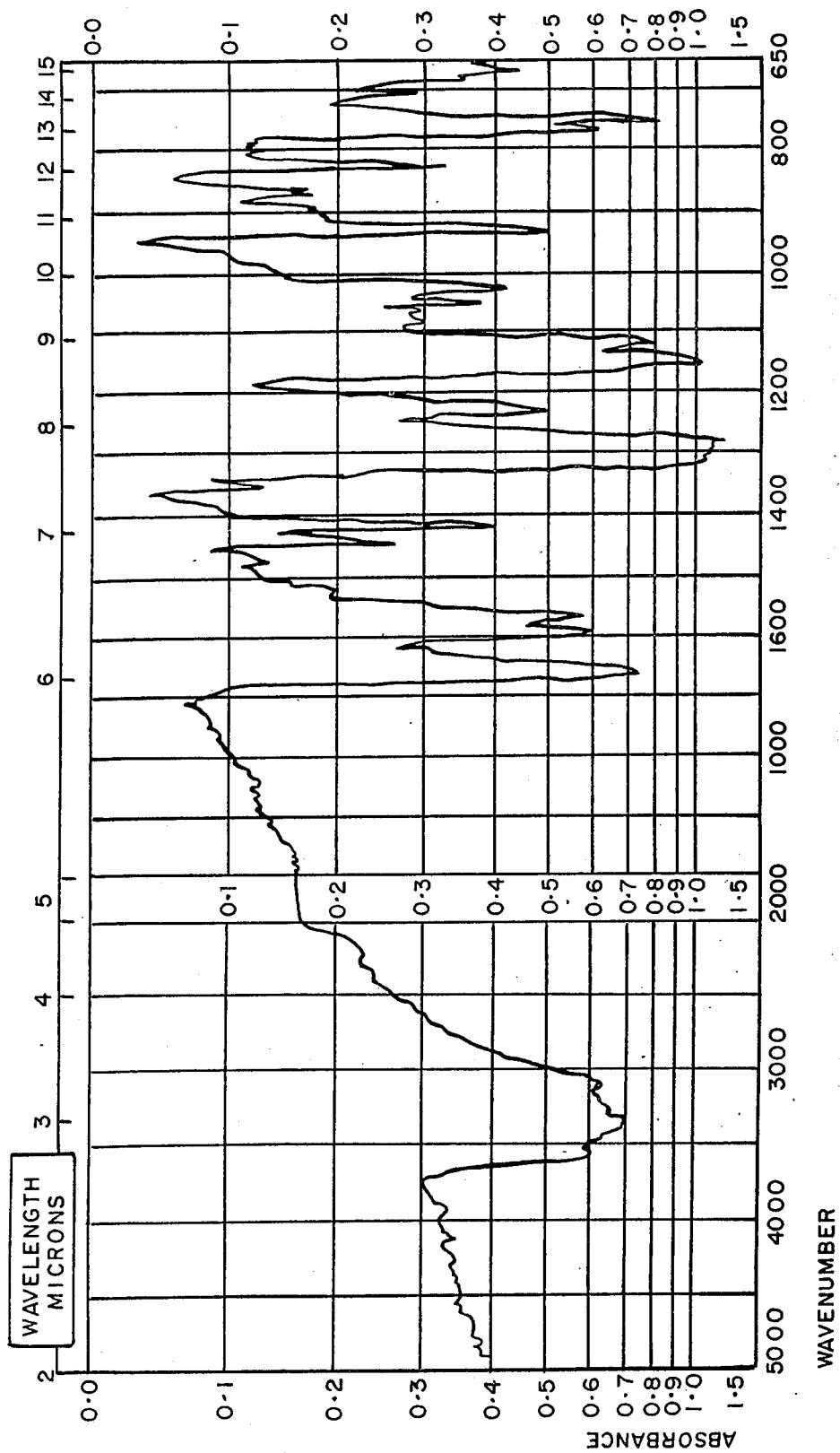
FIG. 1 is the infra-red spectrum for the compound described in Example 17C.

To a mixture of benzene sulphonyl chloride (redistilled) (100.0 g.) and p-xylene (260 ml), vigorously stirred and heated to 40° C, was added aluminum chloride (135 g.) portionwise over 20 minutes. The temperature of the reaction was kept between 55° and 60° C during the addition by means of an ice-bath. The reaction was maintained at 60° C for a further 45 minutes, cooled and decomposed with ice and concentrated hydrochloric acid. The product separated from the organic layer as a yellow solid. This was filtered off, washed with water, and recrystallised from methanol. The resulting solid was collected by filtration, washed with a little cold methanol, and dried at 95° C to give 2,5-dimethyl diphenyl sulphone melting point 111° C.

B. Preparation of diphenyl sulphone-2,5-dicarboxylic acid 2,5-Dimethyl diphenyl sulphone (106 g.), concentrated nitric acid (400 ml) and distilled water (400 ml) were placed in a stainless steel autoclave, sealed, stirred and heated to 160° C for a total of 5 hours. The internal pressure rose to ca. 75 atmospheres. After cooling, the crystalline product was collected by filtration, washed well with water, and dried at 100° C. The resulting diphenyl sulphone-2,5-dicarboxylic acid had a melting point of 270°-274° C.

C. Preparation of 3-carboxythioxanthone-10,10-dioxide

Diphenyl sulphone-2,5-dicarboxylic acid (156.8 g.) was stirred with tetraphosphoric acid (ca. 3,300 g.) and phosphorus pentoxide (ca. 330 g.) at 220° to 230° C for 20 minutes, cooled, and poured onto ice-water with stirring. The precipitated solid was filtered off under suction, washed well with water and dried at 100° C. The total product was recrystallised from aqueous dimethyl formamide, filtered at the boil. The product separated as beige crystals. These were first dried at 100° C, then under vacuum at ca. 170° C, to give 3-carboxythioxanthone10,10-dioxide having a melting point of 287°-289° C.

REFERENCE PREPARATION 2 - 2-carboxythioxanthone-10,10-dioxide

A. Preparation of diphenylsulphone-2,4-dicarboxylic acid

Diphenylsulphone-2,4-dicarboxylic acid was obtained (in the manner described above in preparation 1B by the method used for diphenyl-2,5-dicarboxylic acid) as colourless needles from water, m.p. 246° C.

B. Preparation of 2-Carboxythioxanthone-10,10-dioxide

Diphenylsulphone-2,4-dicarboxylic acid (10.5 g) was stirred and heated with polyphosphoric acid (200 g) at 210°-220° C for 15 minutes, cooled, and poured into water. On heating the mixture to 80° C the crude product separated and was filtered off and recrystallised from acetic acid, m.p. 276° C.

REFERENCE PREPARATION 3 - 2-CARBOXYTHIOXANTHONE-10,10-DIOXIDE

A. Preparation of methylthioxanthone (isomer mixture)

To a stirred mixture of concentrated sulphuric acid (300 ml) and toluene (46 ml), o-mercaptobenzoic acid (30 g) was added slowly. The mixture was stirred for 8 hrs. and allowed to stand for a further 10 hrs. After 1 hr. heating on the steam bath the dark red solution was cooled and poured on to ice. The gummy yellow precipitate was filtered off and triturated with 2N aqueous sodium hydroxide. The solid isomer-mixture was filtered off, washed with water, and dried at room temperature in vacuo, m.p. 107°-132° C.

B. Preparation of 2-methylthioxanthone-10,10-dioxide

To the methylthioxanthone isomer mixture (30.3 g) dissolved in warm acetic acid (200 ml) was added 30% hydrogen peroxide (50 ml), and the mixture boiled under reflux for 2.5 hr. On cooling a yellow solid crystallised out, which was filtered off and dried at 110° C m.p 179°–198° C. Recrystallisation from acetic acid gave pure 2-methylthioxanthone-10,10-dioxide, m.p. 201°–203° C.

C. Preparation of 2-carboxythioxanthone-10,10-dioxide

A solution of chromium trioxide (1.50 g) in water (4.0 ml) was added to 2-methylthioxanthone-10,10-dioxide (1.29 g) in acetic acid (25 ml). Sulphuric acid (2.0 ml) was added and the mixture was boiled under reflux for 15 min. The mixture was cooled, and the crystallised product was filtered off, washed with water, and dried at 110° C, m.p. 276° C.

REFERENCE PREPARATION 4 - 3-carboxythioxanthone-10,10-dioxide

A. Preparation of phenylthioterephthalonitrile

To a sodium methoxide solution, prepared by dissolving sodium (1.46 g) in dry methanol (40 ml), was added redistilled thiophenol (6.92 g), and the methanol removed on a rotary evaporator. Dimethyl sulphoxide (50 ml) was added, and to the resulting solution nitroterephthalonitrile (10.38 g) was added. The dark brown solution was heated on the steam bath for 2 hours, then poured on to ice. The precipitated product was filtered off and dried in vacuo at room temperature, m.p. 106° C. Recrystallisation from ethanol gave the pure product, m.p. 111° C.

B. Preparation of phenylthioterephthalic acid

A mixture of phenylthioterephthalonitrile (6.73 g), sodium hydroxide (4.20 g), water (15ml) and ethanol (100 ml) was boiled under reflux. As evolution of ammonia began, sodium salts began to precipitate and water was added to the reaction mixture to keep the salts in solution. After 2 hours the ethanol was allowed to distil off as more water was added to 150 ml. the solution was filtered, and poured on to ice and excess hydrochloric acid. The precipitated product was filtered off, washed with water, and dried at 110° C, m.p. 328°–331° C (sublimes).

C. Preparation of thioxanthone-3-carboxylic acid

Phenylthioterephthalic acid (7.10 g) was heated with polyphosphoric acid (50 g) at 210°–215° C for 2 hr. with occasional stirring. The dark mixture was poured into water and heated to boiling point, and the greenish product filtered off, washed with water, and recrystallised from aqueous dimethylformamide, m.p. 314°–315° C and a second crop on dilution of the half-evaporated acetic acid liquors with water, gave a m.p. 313°–314° C.

D. Preparation of 3-carboxythioxanthone-10,10-dioxide

A mixture of thioxanthone-3-carboxylic acid (0.120 g), acetic acid (6.0 ml) and 30% hydrogen peroxide (0.12 ml) was boiled under reflux for 15 hr. filtered while hot, and allowed to cool. The product crystallised out slowly. It was filtered off and dried at 110° C, m.p. 285°–287° C.

REFERENCE PREPARATION 5 - 3-CARBOXYTHIOXANTHONE-10,10-DIOXIDE

To 3-carboxythioxanthene-10,10-dioxide (0.72 g) (prepared as hereinafter described) in pyridine (20 ml) was added 40% Triton B pyridine solution (3.5 ml), which resulted in the formation of a deep orange colour. Air was passed through the solution for 20 minutes, after which time the solution was pale green. During the reaction interruption of the air flow resulted in the development of a deep blue colour which disappeared when the flow was restarted. This did not occur when the reaction was completed. The solution as poured onto ice and excess hydrochloric acid and the pale yellow product filtered off and dried at 110° C, m.p. 257°–267° C. After two recrystallisations from acetic acid the product had a m.p. of 282°–284° C and its infra-red spectrum was identical with that of an authentic sample of 3-carboxythioxanthone-10,10-dioxide.

REFERENCE PREPARATION 6 - 2,6-DICARBOXYTHIOXANTHONE-10,10-dioxide

To stirred polyphosphoric acid (800 g) at 290° C was added diphenyl sulphone 2,4',5-tricarboxylic acid (56.7 g) (Bennett, Can. J. Chem., 43 1880 (1965); and Bennett and Gauvin, J. Org. Chem., 34 4165 (1969)) and the temperature maintained at 290° C for ½ hour. The mixture was cooled, and decomposed by heating with water. The black solid was filtered off and recrystallized twice from dimethyl formamide, m.p. above 400° C.

REFERENCE PREPARATION 7 - 3-CARBOXYTHIOXANTHONE-10,10-DIOXIDE

3-Carboxythioxanthone-10,10-dioxide (prepared as in Reference Preparation 1) (5.0 g), zinc wool (10.0 g) and mercuric acetate (0.2 g) in acetic acid (100 ml) were brought to the boil and concentrated hydrochloric acid (10 ml) was added. Vigorous evolution of hydrogen chloride occurred at first. After 2 hr., further hydrochloric acid (7 ml), was added and the mixture boiled under reflux for further 4 hr. It was then filtered while hot and poured on to ice and water. The precipitated product was filtered off and dried at 80° C in vacuo, m.p. 229°–248° C. Two recrystallisations from methanol gave the product m.p. 254° C.

EXAMPLE 1

2,7-Dicarboxythioxanthone-10,10-dioxide

A. Preparation of 2,4,4'-Trimethyldiphenyl sulphone

To a stirred mixture of anhydrous aluminium chloride (66.6g.) in m-xylene (100 ml.) at 50° C was added a solution of p-toluene-sulphonyl chloride (50g.) in m-xylene (60 ml.), dropwise. The temperature of the reaction mixture was allowed to rise to 80° C over 1.5 hrs. by external heating, then the mixture was cooled and poured on to ice and hydrochloric acid. The excess xylene was steam-distilled out and the oily product extracted into chloroform, washed with water and sodium bicarbonate solution, dried, and evaporated. Vacuum distillation gave 2,4,4'-trimethyldiphenyl sulphone, b.pt. 181° C. at 0.5 mm.Hg.

B. Preparation of Diphenyl sulphone-2,4,4'-tricarboxylic acid 2,4,4'-Trimethyldiphenyl sulphone (32.0g.) was heated with 35% nitric acid (200 ml.) in an autoclave to 175° C over 1.5 hr. This temperature was maintained for a further 0.75 hr. After cooling the solid product was filtered off, washed with water, recrystallised from aqueous dimethylformamide, and dried at 110° C, giving diphenyl sulphone-2,4,4'-tricarboxylic acid m.pt. 352°–353° C with decomposition.

Found: C 51.47%; H 3.04%; S 8.98%. $C_{15}H_{10}O_8S$ requires: C 51.44%; H 2.88%; S 9.15%.

C. PREPARATION OF 2,7-DICARBOXYTHIOXANTHONE-10,10-DIOXIDE

Diphenyl sulphone-2,4,4'-tricarboxylic acid (8.50g.) was heated with polyphosphoric acid (127g.) at 290° C for 0.5 hr. with stirring. The dark syrup was cooled and decomposed with water overnight. The dark solid product was filtered off and recrystallised twice from dimethylformamide to give 2,7-dicarboxythioxanthone-10,10-dioxide, m.pt. 372°–375° C with decomposition.

Found: C 54.15%; H 2.47%; S 9.51%. $C_{15}H_8O_7S$ requires C 54.24%; H 2.43%; S 9.65%.

EXAMPLE 2

3-Methoxycarbonylthioxanthone-10,10-dioxide.

3-Carboxythioxanthone-10,10-dioxide (2.0g.), thionyl chloride (25 ml.), and dimethylformamide (2 drops) were boiled together under reflux for 1 hr. The solution was evaporated to dryness, and methanol (100 ml.) added. The mixture was heated to boiling and the clear solution filtered and allowed to cool. The product, which crystallised out, was filtered off and recrystallised from methanol to give 3-methoxycarbonyl-thioxanthone-10,10-dioxide, m.pt. 145°–146° C.

Found: C 59.77., H 3.31%; $C_{15}H_{10}O_5S$ requires C 59.60%; H 3.33$.

EXAMPLE 3

3-Carboxy-7-ethylthioxanthone-10,10-dioxide
A. p-Ethylthiophenol

Chlorosulphonic acid (36g) was added with stirring to ethylbenzene (36G) at 10° C. This temperature was maintained by external cooling throughout the addition. When the addition was completed the mixture was poured on to ice and the product extracted into ether. The combined extracts were washed with water, dried with magnesium sulphate and evaporated.

The residual sulphonyl chloride was stirred with 25% sulphuric acid (500 ml) at 0°–5° C. while zinc dust (70g) was added. The mixture was then heated slowly, and at 88° C an exothermic reaction began. The temperature rose until the mixture boiled gently, and the yellow, oily product detached itself from the zinc. It was steam distilled out, extracted into methylene chloride, dried, evaporated and distilled to give p-ethylthiophenol, b.p. 93°–98° C. at 12 mm.Hg.

B. 2-(p-Ethylphenylthio)terephthalic acid

Sodium (2.0g) was dissolved in methanol (60 ml) and p-ethylthiophenol (10.0g) added. The solution was evaporated to dryness and the residue dissolved in dimethylsulphoxide (60 ml). Nitroterephthalonitrile (12.32g) was added and the mixture heated on the steam bath for 3 hr. The mixture was poured onto ice and the crude product extracted into ether. The extracts were evaporated and boiled under reflux with a solution of sodium hydroxide (9.0g) in water (250 ml) for 16 hr. The solution as cooled and extracted with ether to remove some unchanged thiol, and the aqueous solution was poured into excess hydrochloric acid. The precipitated product was filtered off, washed with hot water, and dried at 95° C. in vacuo, giving 2-(p-ethylphenylthio)terephthalic acid. A sample recrystallised from acetic acid decomposed without melting, and was microanalysed: Found: C 63.33%; H 4.80%. $C_{16}H_{14}O_4S$ requires: C 63.56%; H 4.67%.

C. 7-Ethylthioxanthone-3-carboxylic acid 2-(p-Ethylphenylthio)terephthalic acid (19.0g) was heated with concentrated sulphuric acid (150 ml) at 120° C. for 1.5 hr. The solution was cooled and poured on to ice. The product was filtered off, washed with water, and recrystallised from acetic acid giving 7-ethylthioxanthone-3-carboxylic acid, m.p. 261°– 271° C. A sample was further purified by conversion to the acid chloride. The acid (1.09g) was boiled with thionyl chloride (ca. 10 ml) for 1 hr. and the excess thionyl chloride was evaporated off. The residual acid chloride was recrystallised from toluene, then hydrolysed by boiling with excess sodium hydroxide. Acidification gave the acid, which was recrystallised from acetic acid and dried at 156° C, in vacuo, m.p. 276°–284° C, pure by thin layer chromatography.

Found: C 67.51%; H 4.23%. $C_{16}H_{12}O_3S$ requires C 67.59%; H 4.25%.

D. 3-Carboxy-7-ethylthioxanthone-10,10-dioxide

7-Ethylthioxanthone-3-carboxylic acid (0.25g), 30% hydrogen peroxide (0.25 ml) and acetic acid (2.5 ml) were mixed and boiled under reflux for 4 hr. Further acetic acid was added to completely dissolve the product and the boiling solution was filtered and cooled. 3-Carboxy-7-ethylthioxanthone-10,10-dioxide crystallised out and was filtered off and dried m.p. 300°–303° C.

Found: C 60.55%; H 3.85%. $C_{16}H_{12}O_5S$ requires C 60.76%; H 3.82%.

EXAMPLE 4

7-Ethyl-3-(5-tetrazolyl)thioxanthone-10,10-dioxide
A. 3-Cyano-7-ethylthioxanthone 7-Ethylthioxanthone-3-carboxylic acid (6.07g) was boiled under reflux in thionyl chloride (40ml) containing dimethylformamide (1 drop). The thionyl chloride was distilled off and the residual acid chloride treated with 0.880 ammonia (140 ml). The mixture was boiled for 20 minutes, cooled, and the amide filtered off and dried. To a solution of the amide in dimethylformamide (100 ml) cooled to −30° C. was added thionyl chloride (15 ml) in small portions with cooling. When the addition was complete the mixture was allowed to stand at 0° C. for 20 min., poured into water, and the crude 3-cyano-7-ethylthioxanthone filtered off and dried, m.p. 198°– 215° C. A sample recrystallised from acetic acid had m.p. 210°– 216° C.

B. 7-Ethyl-3-(5-tetrazolyl)thioxanthone

3-Cyano-7-ethylthioxanthone (5.3g), sodium azide (1.55g), and ammonium chloride (1.26g) in dimethylformamide were heated at 120° C. for 3 hr., cooled, and poured into dilute hydrochloric acid. The solid precipitate was filtered off and recrystallised twice from acetic acid to yield 7-ethyl-3-(5-tetrazolyl) thioxanthone m.p. 247° C. with decomposition. Found: C 61.92%; H 4.05%; N 18.18%. $C_{16}H_{12}N_4OS$ requires C 62.32%; H 3.92%; N 18.17%.

C. 7-Ethyl-3-(5-tetrazolyl)thioxanthone-10,10-dioxide

7-Ethyl-3-(5-tetrazolyl)thioxanthone (1.0g) in acetic acid (10 ml) and 30% hydrogen peroxide (1.0ml) were boiled under reflux for 2 hr. On cooling, 7-ethyl-3-(5-tetrazolyl) thioxanthone-10,10-dioxide (0.76g.) crystallised out and was filtered off and dried, m.p. 239° C. with decomposition. Found: C 56.46%; H 3.55%; N 16.46%; $C_{16}H_{12}N_4O_3S$ requires C 56.21%; H 3.66%; N 16.47%.

EXAMPLE 5

7-tert.Butyl-3-carboxythioxanthone-10,10-dioxide

A. 2-(p-tert.Butylphenylthio)terephthalic acid

Starting from p-tert.-butylthiophenol (8.30g) and nitroterephthalonitrile (8.65g), 2-(p-tert.-butylphenylthio)terephthalic acid (5.23g), m.p. 325°–326° C, was prepared in the same way as the ethyl analogue. Found: C 65.64%; H 5.83%. $C_{18}H_{18}O_4S$ requires: C 65.43%; H 5.49%.

B. 7-tert.Butylthioxanthone-3-carboxylic acid 2-(p-tert.-Butylphenylthio)terephthalic acid (5.23g) was cyclised by heating with concentrated sulphuric acid (50 ml) on the steam bath for 10 hr. The solution was cooled and diluted with water, and the precipitated product filtered off and recrystallised from ethanol, giving 7-tert.-butylthioxanthone-3-carboxylic acid m.p. 252°– 257° C. A sample recrystallised from toluene followed by a further recrystallisation from acetic acid had a m.p. of 259°– 261° C. Found: C 69.30%; H 5.20%. $C_{18}H_{16}O_3S$ requires C 69.21%; H 5.16%.

C. 7-tert.Butyl-3-carboxythioxanthone-10,10-dioxide 7-tert.-Butylthioxanthone-3-carboxylic acid (1.52g) in acetic acid (15ml) and 30% hydrogen peroxide (3.0ml) was boiled under reflux for 2 hr. On cooling, 7-tert.butyl-3-carboxythioxanthone-10,10-dioxide seaprated and was filtered off and recrystallised, once from acetic acid and once from aqueous ethanol, to give m.p. 259°– 262° C.

Found: C 62.76%; H 4.69%. $C_{18}H_{16}O_5S$ requires C 62.78%; H 4.68%.

EXAMPLE 6

7-tert.Butyl-3-(5-tetrazolyl)thioxanthone-10,10-dioxide

A. 7-tert.Butylthioxanthone-3-carboxamide 7-tert.Butylthioxanthone-3-carboxylic acid (2.0g) was boiled under reflux with thionyl chloride (20 ml) for 30 min. The thionyl chloride was evaporated off and the residue dissolved in hot toluene (25 ml) and decanted from a small quantity of tarry impurity. Evaporation gave the acid chloride which was treated with 0.880 ammonia (50 ml), warmed on the water bath, filtered and washed with water to yield after drying 7-tert.butylthioxanthone-3-carboxamide, m.p. 274°–275° C.

B. 7-tert.Butyl-3-cyanothioxanthone 7-tert.Butylthioxanthone-3-carboxamide (1.67g) was dissolved in hot dimethylformamide (15ml) and cooled to −60° C. Thionyl chloride (3.0ml) was added and the mixture allowed to warm to 0° C. in an ice bath for 20 min., poured into water, and 7-tert.butyl-3-cyanothioxanthone filtered off and dried, m.p. 181°– 184° C.

C. 7-tert.Butyl-3-(5-tetrazolyl)thioxanthone

A mixture of 7-tert.butyl-3-cyanothioxanthone (1.25g), sodium azide (0.31g), ammonium chloride (0.25g) and dimethylformamide (15ml) was heated at 125°– 130° C for 4 hr., cooled, and poured into dilute hydrochloric acid. The yellow precipitated product was filtered off and recrystallised from dimethylformamide to yield 7-tert.butyl-3-(5-tetrazolyl)thioxanthone, m.p. 277° C. with decomposition. Found: C 64.33%; H 5.11%; N 16.68%. $C_{18}H_{16}O_4OS$ requires: C 64.27%; H 4.80%; N 16.66%.

D. 7-tert.Butyl-3-(5-tetrazolyl)thioxanthone-10,10-dioxide 7-tert.Butyl-3-(5-tetrazolyl)thioxanthone (1.0g) was boiled under reflux with acetic acid (10ml) and 30% hydrogen peroxide (1.0ml) for 2 hr., diluted with water to saturation point at the boil, filtered and cooled. 7-tert.Butyl-3-(5-tetrazolyl)thioxanthone-10,10-dioxide crystallised out and was filtered off and recrystallised from dimethylformamide, m.p. 228° C. with decomposition. Found: C 58.28%; H 4.47%; N 14.74%. $C_{18}H_{16}N_4O_3S$ requires C 58.68%; H 4.38%; N 15.21%.

EXAMPLE 7

4-Carboxythioxanthone-10,10-dioxide

A. Cupric o-chlorobenzoate o-Chlorobenzoic acid (31.3g) was dissolved in a solution of sodium hydroxide (8.0g) in water (250 ml) and the warmed solution filtered and treated with a solution of cupric sulphate pentahydrate (25.0g) in water (200 ml). The precipitated blue-green solid was filtered off, washed with water, and dried to give cupric chlorobenzoate, m.p. 259° C. with decomposition.

B. Cupric complex of thiosalicylic acid

Thiosalicylic acid (30.8g) was added to a solution of sodium hydroxide (16.0g) in water (300 ml) and to the resulting solution was added a solution of cupric sulphate pentahydrate (50.0g) in water (30 ml). The precipitated black complex was filtered off, washed with water and ethanol, and dried.

C. Diphenyl sulphide 2,2'-dicarboxylic acid

A mixture of cupric o-chlorobenzoate (28.2g), thiosalicylic acid cupric complex (32.4g) and dimethylformamide (450 ml) was boiled under reflux for 2 hr. The dull green precipitate was filtered from the cooled mixture and allowed to stand overnight in 2N. hydrochloric acid (200 ml). The product was filtered off, washed with water, and heated with normal sodium hydroxide solution (400 ml). A black residue was filtered off and the filtrate acidified to precipitate diphenyl sulphide 2,2'-dicarboxylic acid which was filtered off, washed with water and dried, m.p. 232°– 234° C. A sample recrystallised from acetic acid had m.p. 236° C. Found: C 61.42%; H 3.72%. $C_{14}H_{10}O_4S$ requires C 61.32%, H 3.68%.

D. Thioxanthone-4-carboxylic acid

Diphenyl sulphide 2,2'-dicarboxylic acid (19.0g) was heated on a steam bath with concentrated sulphuric acid (150 ml) for 1 hr., and the dark solution cooled and poured into water. The yellow precipitate was filtered off, washed well with water and dried, giving thioxanthone-4-carboxylic acid. A sample recrystalised from dimethylformamide, then acetic acid, had m.p. 353° C (with sublimation). Found: C 65.47%; H 3.14%. $C_{14}H_8O_3$ requires: C 65.74%; H 3.28%.

E. 4-Carboxythioxanthone-10,10-dioxide

Thioxanthone-4-carboxylic acid (5.0g), acetic acid (100 ml) and 30% hydrogen peroxide (5.0ml) were boiled under reflux for 1 hr. On cooling, 4-carboxythioxanthone-10,10-dioxide crystallised out and was filtered off and dried, m.p. 237° C. Found: C 58.14%; H 2.95%. $C_{14}H_8O_5$ requires C 58.34%; H 2.80%.

EXAMPLE 8

4-(5-Tetrazolyl)thioxanthone-10,10-dioxide

A. 4-Cyanothioxanthone-10,10-dioxide

4-Carboxythioxanthone-10,10-dioxide (2.10g) was boiled with thionyl chloride (15 ml) containing 1 drop of dimethylformamide for 10 min., cooled and evaporated. The residual acid chloride was treated with 0.880 ammonia (30 ml.) and warmed on a steam bath for 10 min. The solid amide (1.75g) was filtered off and dried (m.p. 252°–254° C). It was dissolved in hot dimethylformamide (30.ml.) and cooled to −70° C. Thionyl chloride (4.0 ml) was added and the solution stood in an ice-bath for 30 min. The mixture was poured into cold water and 4-cyanothioxanthone filtered off, washed with water and dried, m.p. 289°–291° C.

B. 4-(5-Tetrazolyl)thioxanthone-10,10-dioxide

4-Cyanothioxanthone-10,10-dioxide (1.35g), sodium azide (0.39g) ammonium chloride (0.32g) and dimethylsulphoxide were heated together at 125°–130° C. for 6.5 hr. The mixture was cooled, poured into dilute hydrochloric acid and the precipitated product filtered off. It was warmed with 1% sodium bicarbonate solution, filtered, and the filtrate acidified with dilute hydrochloric acid. 4-(5-Tetrazolyl)thioxanthone-10,10-dioxide was filtered off and recrystallised from acetic acid, m.p. 271° C. with decomposition. Found: C 53.50%; H 2.70%; N 18.04%. $C_{14}H_8N_4O_3S$ requires C 53.85%; H 2.58%; N 17.95%.

EXAMPLE 9

3-((2-Carboxyethyl)-5-tetrazolyl)thioxanthone-10,10-dioxide

Ethyl 3-bromopropionate (9.05 g) in acetone (70 ml) was added to 3-(5-tetrazolyl)thioxanthone-10,10-dioxide (15.6 g) and sodium hydroxide (2.0 g) in water (15 ml). The mixture was boiled under reflux for 8 hr. On cooling the ester product crystallised out and was filtered off, washed with dilute sodium bicarbonate solution, and recrystallised from ethanol, m.p. 143°–145° C. The ester (4.5 g) was boiled with a mixture of concentrated hydrochloric acid (40 ml) and acetic acid (120 ml) for 3 hr. On cooling, 3-((2-carboxyethyl)-5-tetrazolyl)thioxanthone-10,10-dioxide crystallised out and was filtered off and washed with water, m.p. 206°–207° C. Found: C, 53.10%; H, 3.22%; N, 14.59%. $C_{17}H_{12}N_4O_5S$ requires C, 53.12%; H, 3.15%; N, 14.58%.

EXAMPLE 10

3-(2-Methyl-5-tetrazolyl)thioxanthone-10,10-dioxide

To a solution of sodium ethoxide in ethanol (20 ml) (prepared from 0.46 g sodium) was added 3-(5-tetrazolyl)thioxanthone-10,10-dioxide (6.24g). Methyl iodide (2.84 g) was added and the mixture boiled under reflux for 2 hr. During the reflux period a yellow product was deposited. On cooling it was filtered off, washed with water and recrystallised twice from acetic acid to give 3-(2-methyl-5-tetrazolyl)thioxanthone-10,10-dioxide as yellow needles, m.p. 204°–205° C.

Example 11

3(2-(3-Dimethylaminopropyl)-5-tetrazolyl) thioxanthone-10,10-dioxide

Sodium (0.69 g) was dissolved in ethanol (45 ml) and 3-(5-tetrazolyl)thioxanthone-10,10-dioxide (4.68 g) was added. 3-Dimethylaminopropyl chloride hydrochloride (2.37 g) was added to the mixture, which was then stirred and boiled under reflux for 2.5 hr. On cooling some solid separated, which was filtered off and discarded. Overnight yellow crystals of 3-(2-(3-dimethylaminopropyl)-5-tetrazolyl)thioxanthone-10,10-dioxide separated and were filtered off and recrystallised from ethanol, m.p. 141°–142° C.

Found: C, 57.96%; H, 5.00%; N, 17.58%. $C_{19}H_{19}N_5O_3S$ requires C, 57.41%; H, 4.82%; N, 17.62%.

Example 12

3-(2-Carboxymethyl-5-tetrazolyl)thioxanthone-10,10-dioxide

Sodium (0.46 g) was dissolved in ethanol (20 ml) and 3-(5-tetrazolyl)thioxanthone-10,10-dioxide (6.24g) was added. Ethyl bromoacetate (3.34 g) was added to the mixture, which was boiled under reflux for 1.5 hr. The ester intermediate was deposited during this time, and after cooling was filtered off, washed with water and dried, m.p. 194°–195° C. The ester was boiled with concentrated hydrochloric acid (40 ml) and acetic acid (120 ml) for 2 hr. On cooling 3-(2-carboxymethyl-5-tetrazolyl)thioxanthone-10,10-dioxide crystallised out, and was filtered off, recrystallised from acetic acid, and dried, m.p. 252° C. with decomposition.

Found: C, 52.09%; H, 2.73%; N, 15.10%. $C_{16}H_{10}N_4O_5S$ requires C, 51.90%; H, 2.72%; N, 15.13%.

Example 13

2-Carboxy-6-(5-tetrazolyl)thioxanthone-10,10-dioxide

7-Methyl-3-(5-tetrazolyl)thioxanthone-10,10-dioxide (0,78g) was suspended in acetic acid (50 ml) and chromium trioxide (0.98g) in water (2.0 ml) added dropwise, followed by concentrated sulphuric acid (0.5 ml) added dropwise. The mixture was heated on the steam bath for 1 hr., then boiled under reflux for 4 hr. Further chromium trioxide (0.98g) was added and the mixture boiled for a further 16 hr. The green solution was diluted with water, and the precipitated solid filtered off and washed with water. The solid was boiled with acetic acid (200 ml), filtering at the boil.

Insoluble material (0.26g) was removed, and on cooling and standing, 2-carboxy-6(5-tetrazolyl)thioxanthone-10,10-dioxide separated. This was filtered off, washed with water and dried. The dipotassium salt was obtained by dissolving the solid in the minimum possible quantity of warm saturated potassium bicarbonate solution. On cooling in an ice bath the dipotassium salt trihydrate separated and was filtered off, washed with a little ice-water and dried.

Found: C, 37.04%; H, 2.24%; N, 11.31%. $C_{15}H_6K_2N_4O_5S.3H_2O$ requires: C, 37.03%; H, 2.47%; N, 11.52%.

Example 14

3-Carboxy-7-chlorothioxanthone-10,10-dioxide

A. p-Chlorophenylthioterephthalonitrile

Sodium (1.15g) was dissolved in dry methanol (35 ml), and p-chlorothiophenol (7.23g) was added. The solution was evaporated and dimethylsulphoxide (40 ml) added to the residue, followed by nitroterephthalonitrile (8.65g). The solution was heated on a steam bath for 30 mins., poured into cold water, and the precipitated p-chlorophenylthioterephthalonitrile filtered off, washed with water, and dried, m.p. 162°–165° C. A sample recrystallised from isopropanol had m.p. 167°–168° C.

B. p-Chlorophenylthioterephthalic acid p-Chlorophenylthioterephthalonitrile (8.0g) was boiled under reflux with sodium hydroxide (4.55g) in water (150 ml) for 16 hr. Filtration of the hot solution gave the diamide, m.p. 308°–310° C., and acidification of the filtrate with hydrochloric acid yielded p-chlorophenylthioterephthalic acid, m.p. 346°–347° C. A sample recrystallised from acetic acid had m.p. 353°–354° C.

C. p-Chlorophenylsulphonylterephthalic acid p-Chlorophenylthioterephthalic acid (2.0g), acetic acid (20 ml) and 30% hydrogen peroxide (2.0 ml) were boiled together under reflux for 30 min. Further peroxide (2.0 ml) was added and boiling continued for a further 30 min. The solution was partially evaporated, diluted with water, and the precipitated p-chlorophenylsulphonylterephthalic acid filtered off and recrystallized from aqueous acetic acid m.p. 270°–272° C.

D. 3-Carboxy-7-Chlorothioxanthone-10,10-dioxide p-Chlorophenylsulphonylterephthalic acid (5.0 g) was dissolved in concentrated sulphuric acid (50 ml) and heated at 240° C. for 2 hr. The solution was cooled, poured on to ice, and the precipitated 3-carboxy-7-chlorothioxanthone-10,10-dioxide filtered off, washed with water, and recrystallised from acetic acid, m.p. 352°–355° C.

Found: C, 52.06%; H, 2.16%; $C_{14}H_7ClO_5S$ requires: C, 52.10%; H, 2.19%.

EXAMPLE 15

7-Chloro-3-(5-tetrazolyl)thioxanthone-10,10-dioxide

A. 2-(p-Chlorophenylthio)-4-(5-tetrazolyl)benzonitrile p-Chlorophenylthioterephthalonitrile (3.28g), sodium axide (0.78g), ammonium chloride (0.65g) and dimethylformamide (30 ml) were heated together on the steam bath for 16 hr. The mixture was cooled and poured into dilute hydrochloric acid. The oil which precipitated and solidified slowly was dissolved in sodium bicarbonate solution and the solution extracted with chloroform to remove unchanged starting material. Acidification of the aqueous solution precipitated 2-(p-Chlorophenylthio)-4-(5-tetrazolyl)benzonitrile, decomposes at 222° C.

B. 2-(p-Chlorophenylthio)-4-(5-tetrazolyl)benzoic acid 2-(p-Chlorophenylthio)-4-(5-tetrazolyl)benzonitrile (3,24g) was dissolved in 0,5N sodium hydroxide solution (150 ml) and boiled under reflux for 16 hr. The warm solution was acidified with hydrochloric acid and the precipitated 2-(p-chlorophenylthio)-4-(5-tetrazolyl)benzoic acid filtered off, washed with water and dried, decomposes at 245° C.

C. 7-Chloro-3-(5-tetrazolyl)thioxanthone 2-(p-Chlorophenylthio)-4-(5-tetrazolyl)benzoic acid (3.41g) was heated with polyphosphoric acid (70g) on a steam bath for 1 hr. The reaction mixture was decomposed by warming with water, and the product filtered off, washed with water, recrystallised from dimethylformamide, and dried at 156° C. in vacuo, giving 7-chloro-3-(5-tetrazolyl)thioxanthone, decomposes without melting.

Found: C, 53.75%; H, 2.27%; N, 17.93%. $C_{14}H_7ClN_4OS$ requires: C, 53.42%; H, 2.24%; N, 17.80%.

D. 7-Chloro-3-(5-tetrazolyl)thioxanthone-10,10-dioxide

7-Chloro-3-(5-tetrazolyl)thioxanthone (1.21g), acetic acid (20 ml) and 30% hydrogen peroxide (3.5 ml) were boiled together under reflux for 2.5 hr. The solid did not pass into solution completely. The mixture was cooled and the solid product filtered off and recrystallised twice from dimethylformamide to give 7-chloro-(3-(5-tetrazolyl)thioxanthone-10,10-dioxide, decomposes without melting.

Found: C, 48.65%; H, 2.10%, N, 15.85%. $C_{14}H_7ClO_3S$ requires: C, 48.49%; H, 2.03%; N, 16.16%.

EXAMPLE 16

3-Carboxy-7-methoxythioxanthone-10,10-dioxide

A. p-Methoxyphenylthioterephthalonitrile

Sodium (4.66g) was dissolved in methanol (120 ml) and p-methoxythiophenol (28,3g, prepared by the method used for p-ethylthiophenol) was added. The solution was evaporated to dryness and the residue dissolved in dimethylsulphoxide (200 ml). Nitroterephthalonitrile (34.9g) was added, and the resulting solution heated on the steam-bath for 1 hr. On diluting the cooled solution with water, p-methoxyphenylthioterephthalonitrile crystallised out and was filtered off and dried. A smaple recrystallised from ethanol had m.p. 126°–127° C.

B. p-Methoxyphenylthioterephthalic acid p-Methoxyphenylthioterephthalonitrile (1.60g), sodium hydroxide (0.91g) and water (30 ml) was boiled together under reflux for 8 hr. A solid residue was filtered from the reaction mixture and the filtrate acidified with hydrochloric acid. p-Methoxyphenylthioterephthalic acid was filtered off, washed with water and dried. A sample recrystallised from acetic acid had m.p. 326° C.

C. 7-Methoxythioxanthone-3-carboxylic acid p-Methoxyphenylthioterephthalic acid (13.4g) was heated with polyphosphoric acid (260g) at 120° C. for 2 hr., then at 140° C. for 4 hr. The reaction mixture was decomposed by warming with water and the solid product was filtered off and washed well with water. Recrystallisation from acetic acid gave impure 7-methoxythioxanthone-3-carboxylic acid, m.p. >360° C.

D. 3-Carboxy-7-methoxythioxanthone-10,10-dioxide

7-Methoxythioxanthone-3-carboxylic acid (1.50g), acetic acid (25 ml) and 30% hydrogen peroxide (1.0 ml) were boiled together under reflux for 2 hr. Some solid remained undissolved. The mixture was cooled and filtered, and the residue recrystallised first from acetic acid, then from dimethylformamide to give 3-carboxy-7-methoxythioxanthone-10,10-dioxide, m.p. 324°–327° C.

Found: C, 56.33%; H, 3.15%; $C_{15}H_{10}O_6S$ requires: C, 56.61%; H, 3.17%.

Example 17

3-(5-Tetrazolyl)thioxanthone-10,10-dioxide sodium salt

A. Preparation of 3-Carbamoylthioxanthone-10,10dioxide

3-Carboxythioxanthone-10,10-dioxide (15.0 g) (prepared as in Reference Preparation η) was refluxed with thionyl chloride (100 ml) for 2 hours. The clear solution was evaporated under reduced pressure to give a solid residue. Carbon tetrachloride was added and re-evaporated, repeating several times, to remove any remaining thionyl chloride. The resulting solid was added portionwise to aqueous ammonia (75 ml water, 75 ml of .880 ammonia) with stirring, stirred for two hours, and the resulting pink-coloured solid was filtered, washed with water and dried at 100° C, then at 110° C under vacuum. The resulting 3-carbamoylthioxanthone 10,10-dioxide when recrystallised from dimethyl formamide had a melting point of 292° C.

B. Preparation of 3-cyanothioxanthone-10,10-dioxide

3-Carbamoylthioxanthone-10,10-dioxide (32.5 g) was dissolved in dimethyl formamide (ca. 1 litre) and cooled to −10° C in a solid carbon dioxide ethanol bath. Thionyl chloride (80 ml) was then added dropwise over 0.5 hour, maintaining the internal temperature at −5° to −10° C. Stirring was continued at this temperature for a further 2 hours. The reaction mixture was then poured into ice-water. The precipitated solid was filtered off, washed well with water, and dried at 100° C. The resulting 3-cyanothioxanthone-10,10-dioxide had a melting point of 282–283° C.

C. Preparation of 3-(5-tetrazolyl)thioxanthone-10,10-dioxide sodium salt

3-Cyanothioxanthone-10,10-dioxide (28.2 g), sodium azide (7.5 g), ammonium chloride (6.7 g) and dimethylformamide (180 ml) were warmed together on a steam bath for a total of 7 hours, left to stand for two days at room temperature, and then poured onto ice and concentrated hydrochloric acid. The cream-coloured precipitate was filtered off and warmed with N aqueous sodium hydroxide solution (110 ml) on the steam bath. The mixture was filtered from insoluble material, and the filtrate deposited the required product on cooling. This was filtered off, washed with a little cold water, and dried under vacuum at ca. 90° C, to give 3-(5-tetrazolyl)thioxanthone-10,10-dioxide sodium salt) which when dispersed in a potassium bromide disc had the infra-red spectrum shown in FIG. 1. (Unicam SP200 - Unicam Instruments Ltd., Cambridge)

Example 18

3-(5-Tetrazolyl)thioxanthone-10,10-dioxide

The sodium salt of Example 17(2.0 g) was dissolved in distilled water (75 ml) with slight warming. The yellow/orange solution was then acidified to congo red with 2N hydrochloric acid to precipitate the required product. This was filtered off, washed with water, and recrystallised from boiling glacial acetic acid, filtering at the boil. The resulting yellow crystals were collected by filtration, washed with a little cold glacial acetic acid, and finally dried under vacuum at 140° C. The product, 3-(5-tetrazolyl) thioxanthone-10,10-dioxide had a melting point 260°–262° C (decomposition).

Example 19

3-(5-Tetrazolyl)thioxanthone-10,10-dioxide

A. Preparation of thioxanthone-3-carboxamide

Thioxanthone-3-carboxylic acid (3.00 g) (prepared as described therein) was refluxed with thionly chloride (20 ml) for 45 min. The excess thionyl chloride was evaporated off, and the residual acid chloride dissolved in methylene chloride (70 ml) and added to 0.880 ammonia solution (70 ml). The precipitated amide was filtered off and dried at 110° C, m.p. 287°–291° C.

B. Preparation of 3-Cyanothioxanthone

Thioxanthone-3-carboxamide (3.09 g) was dissolved in hot dimethylformamide (50 ml) and cooled to −30° C, whereupon the solid starting material separated. Thionyl chloride (7.5 ml) was added dropwise over 10 min. to the stirred mixture at −20° to −30° C, and the mixture was then stirred in an ice bath for 2 hours, during which time the temperature rose to 5° C. Some residual solid was left. The mixture was poured into ice-water and the greenish-yellow product was filtered off and dried at 110° C, m.p. 255°–256° C (softens 251° C).

C. Preparation of 3-(5-Tetrazolyl)thioxanthone

A mixture of 3-cyanothioxanthone (2.56 g), sodium azide (0.84 g) and ammonium chloride (0.70 g) in dimethylformamide (20 ml) was heated on a steam bath for 5 hrs. The nitrile dissolved after 2 hr., at the same time a precipitate of the product forming. Much solid crystallised out on cooling. The reaction mixture was poured into excess dilute hydrochloric acid, and the yellow precipitate was filtered off and washed with water. It was dissolved in dilute aqueous sodium hydroxide, filtered and reprecipitated with dilute hydrochloric acid. The product was filtered off and dried at 110° C, and then recrystallised from dimethylformamide and dried at 154° C/15mm. Hg, decomposes 290° C.

D. Preparation of 3-(5-Tetrazolyl)thioxanthone-10,10-dioxide 3-(5-Tetrazolyl)thioxanthone (0.40 g) was boiled with 30% hydrogen peroxide (0.80 ml) in acetic acid (30 ml) for 1 hr. The resulting colourless solution was diluted with an equal volume of water, filtered while hot and cooled to yield the 10,10-dioxide, m.p, 257° C (decomposition).

Example 20

3-Carboxy-7-methylthioxanthone-10,10-dioxide

A. Preparation of 2-(p-tolylthio)terephthalonitrile

To a solution sodium methoxide (made from sodium (2.18 g) in methanol (50 ml) was added p-toluene thiol (11.8 g). The solution was evaporated to dryness and the residual sodium salt dissolved in dry dimethylsulphoxide (150 ml). Nitroterephthalonitrile (15.56 g) was added and the resulting dark solution was heated on the steam bath for 30 min., then poured into water. The precipitated product was filtered off, washed with water and dried at room temperature in vacuo, m.p. 155° C.

B. Preparation of 2-(p-tolylthio)terephthalic acid.

The dinitrile (14.5 g) was dissolved in ethanol (100 ml) and sodium hydroxide (9.5 g) in water (100 ml) was added. The mixture was boiled under refluxed for 30 min., the ethanol distilled off and the residual solution filtered and boiled for a further 7 1/2 hours. It was then poured on to excess hydrochloric acid and ice and the precipitated acid filtered off, washed with water, and dried at 100° C, m.p. 326° C (decomposes).

C. Preparation of 7-methylthioxanthone-3-carboxylic acid 2-)p-Tolylthio)terephthalic acid (13.5 g) was stirred and heated with polyphosphoric acid (330 g) at 100° C for 3 hours. The mixture was decomposed with water and the ochre-coloured acid filtered off and recrystallised from acetic acid, m.p. 321°–323° C.

D. Preparation of 3-carboxy-7-methylthioxanthone-10,10-dioxide

7-Methylthioxanthone-3-carboxylic acid (4.0 g) was dissolved in acetic acid (400 ml) and 30% hydrogen peroxide (15 ml) was added. The mixture was boiled under reflux for 2 hours and cooled. The product, which crystallised out, was filtered off and dried at 110° C, m.p. 357° C (decomposes). Example 21 - 3-Carbamoyl-7-Methylthioxanthone-10,10-dioxide 3-Carboxy-7-methylthioxanthone-10,10dioxide (0.99 g) was boiled with thionyl chloride (10 ml) containing 1 drop dimethyl formamide for 2 hours. The solution was evaporated to dryness and the solid acid chloride residue added to 15% ammonia solution (30 ml) with stirring. After 1 hour the amide was filtered off, washed with water, and dried at 100°C, m.p. 305° C (decomposes).

Example 22 -
7-Methyl-3-(5-tetrazolyl)thioxanthone-10,10-dioxide

A. Preparation of 3-Cyano-7-methylthioxanthone-10,10-dioxide

The amide (0.79 g) of Example 21 was added to a mixture of dimethyl formamide (100 ml) and thionyl chloride (2.0 ml) at −10° C, and stirred at −10° C for 2 hrs. The mixture was poured on to ice-water and the precipitated product filtered off and washed with water, recrystallised from dimethylformamide, and dried at 155° C/15 mm. Hg, m.p. 290° C (decomposes).

B. Preparation of 7-methyl-3-(5-tetrazolyl)thioxanthone-10, 10-dioxide

3-Cyano-7-methylthioxanthone-10,10-dioxide (0.36 g), sodium azide (0.091 g), ammonium chloride (0.081 g) and dimethyl formamide (5.0 ml) were heated together on the steam bath for 7 hrs., poured on to ice and hydrochloric acid, and the precipitated tetrazole filtered off, washed with water and recrystallised from acetic acid, m.p. 267° C (decomposes).

EXAMPLE 23

3-Carboxythioxanthone-10,10-dioxide sodium salt

3-Carboxythioxanthone-10,10-dioxide (2.88 g: 10 mmole) was dissolved in N sodium hydroxide (10 ml) to give a dark-coloured solution, which was then evaporated to dryness under reduced pressure.

Figure 2:
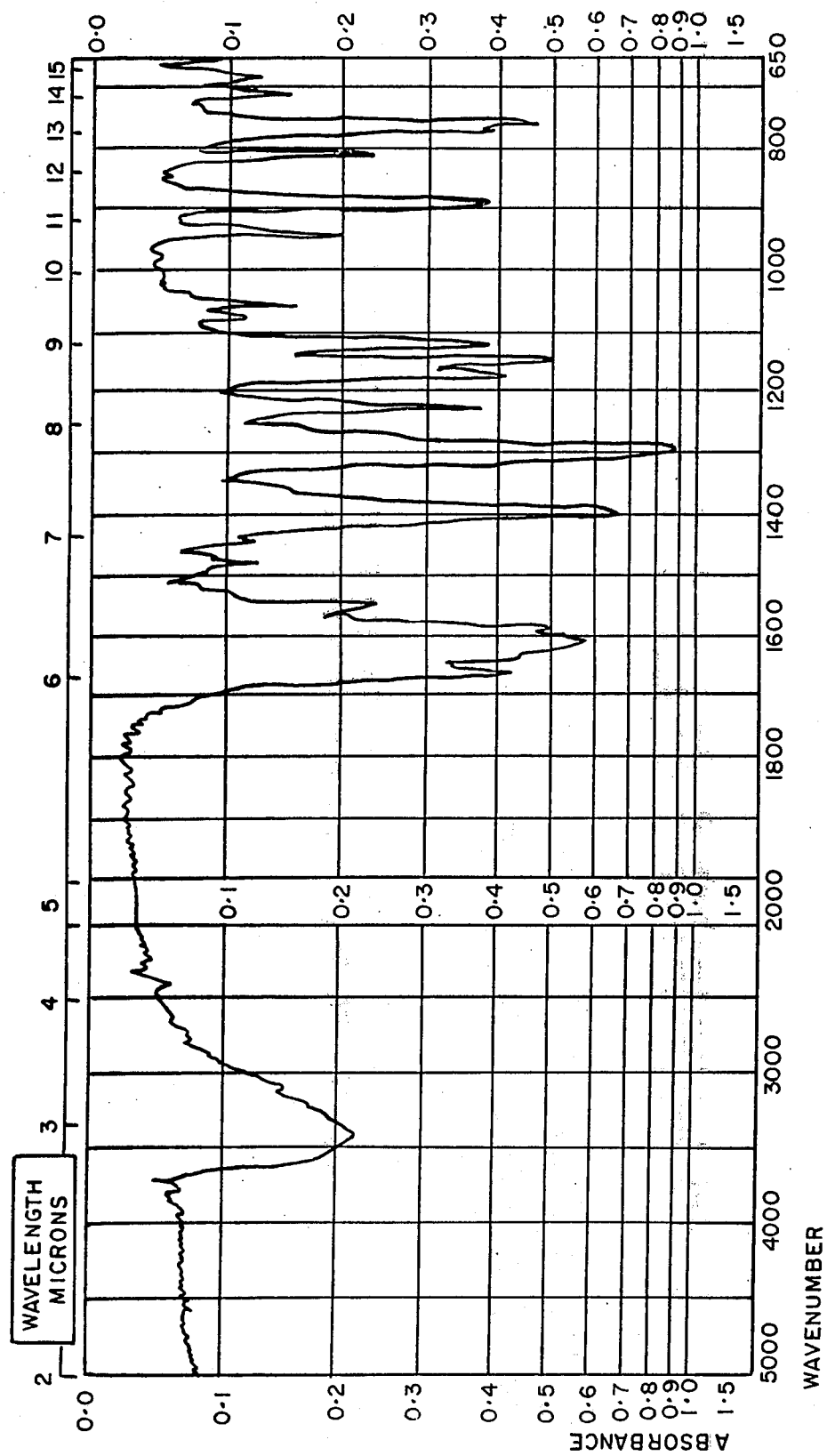
FIG. 2 is the infra-red spectrum for the compound described in Example 23.

The solid residue was recrystallised from aqueous ethanol and the product dried at 100° C. A second crop was obtained from the recrystallisation liquors on standing. This was filtered off, and dried at 100° C to yield the product, 3-carboxythioxanthone-10,10-dioxide sodium salt (hydrated) Further drying at 156° C./20m.m. Hg gave the anhydrous compound having the infra red spectrum shown in FIG. 2 when dispersed in a potassium bromide disc (Unicam SP 200 (Unicam Instruments Ltd., Cambridge)).

EXAMPLE 24

3-(5-Tetrazolyl)thioxanthone-10,10-dioxide

A. 2-Phenylthio-4-(5-tetrazolyl)benzonitrile

Phenylthioterephthalonitrile (2.36g), sodium azide (0.65g) and ammonium chloride (0.54g) were heated in dimethylformamide (25 ml) on the steam bath for 16 hrs. An insoluble deposit of sodium chloride formed. The reaction mixture was poured into hydrochloric acid (50 ml, 0.6 normal). When the oily precipitate had crystallised it was filtered off, recrystallised from acetic acid, and dried in vacuo over potassium hydroxide pellets, m.p. 187° C.

B. 2-Phenylthio-4-(5-tetrazolyl)benzoic acid

2-Phenylthio-4-(5-tetrazolyl)benzonitrile (1.89g) was dissolved in 0.5 normal sodium hydroxide solution (100 ml) and boiled for 9.5 hrs. The solution was poured on to ice and excess hydrochloric acid, and the precipitated product filtered off and recrystallised from acetic acid, m.p. 239°–240° C.

C. 2-Phenylsulphonyl-4-(5-tetrazolyl)benzoic acid

2-Phenylthio-4-(5-tetrazolyl)benzoic acid (4.20g), acetic acid (100 ml) and 30% hydrogen peroxide (20 ml) were boiled under reflux for 2 hr. The solution was cooled and evaporated and the residue recrystallised from acetonitrile, with which the product formed a complex stable at 80° C./20 mm. Hg. The product was obtained pure by drying at 156° C./20 mm. Hg, the 2-phenylsulphonyl-4-(5-tetrazolyl)benzoic acid having m.p. 250° C. with decomposition.

D. 3-(5-Tetrazolyl)thioxanthone-10,10-dioxide

2-Phenylsulphonyl-4-(5-tetrazolyl)benzoic acid (200 mg) was heated with concentrated sulphuric acid (10 ml) for 5 hr. at 120° C. After cooling and dilution with water, a solid product seperated and was filtered off, washed with water, and recrystallised from acetic acid to give 3-(5-tetrazolyl)thioxanthone-10,10-dioxide, identified by its infrared spectrum.

EXAMPLE 25

3-Carboxythioxanthone-10,10-dioxide ethanolamine salt

To 3-carboxythioxanthone-10,10-dioxide (2.88g) was added a solution of ethanolamine (0.61g) in water (10 ml). The solution was filtered and evaporated to dryness, leaving a residue of 3-carboxythioxanthone-10,10-dioxide ethanolamine salt, m.p. 195° C. with decomposition. Found: C, 54.98%; H, 4.33%; N, 3.93%. $C_{16}H_{15}NO_6S$ requires C, 55.01%; H, 4.33%; N, 4.01%.

EXAMPLE 26

7-Methoxy-3-(5-tetrazolyl)thioxanthone-10,10-dioxide

A. 7-Methoxy-3-(5-tetrazolyl)thioxanthone

7-Methoxythioxanthone-3-carboxylic acid (6.0g) was boiled with thionyl chloride (40 ml) and dimethylformamide (1 drop) for 1 hr., filtered and evaporated. The residual acid chloride was recrystallised from toluene and treated with 0.880 ammonia (40 ml) boiling gently for 40 min. The amide (m.p. 299°–301° C.) was filtered off, dried, dissolved in hot dimethylformamide (50 ml) and cooled to −30° C. Thionyl chloride (5.0 ml) was added with stirring, and the temperature maintained at −30° C. for 30 min. The solution was poured onto ice and the nitrile (m.p. 251°–255° C.) filtered off and dried.

The nitrile, sodium azide (0.38g), ammonium chloride (0.31g) and dimethylformamide (20 ml) were heated together at 130° C. for 3 hr., cooled and diluted with sodium hydroxide solution. The solution was filtered and acidified with hydrochloric acid. j The product was filtered off and recrystallised from acetic acid, to yield 7-methoxy-3-(5-tetrazolyl)thioxanthone m.p. >350° C.

Found: C, 57.70%; H, 3.39%; N, 17.97%. $C_{15}H_{10}N_4O_2S$ requires C, 58.06%; H, 3.25%; N, 18.06%.

B. 7-Methoxy-3-(5-tetrazolyl)thioxanthone-10,10-dioxide

7-Methoxy-3-(5-tetrazolyl)thioxanthone (0.50g), acetic acid (25 ml) and 30% hydrogen peroxide (1.0 ml) were boiled together under reflux for 45 min. On cooling, 7-methoxy-3-(5-tetrazolyl) thioxanthone-10,10-dioxide separated, and was filtered off and recrystallised from acetic acid, m.p. 253° C. with decomposition.

Found: C, 52.51%; H, 3.03%; N, 16.09%. $C_{15}H_{10}N_4O_4S$ requires C, 52.64%; H, 2.95%; N, 16.37%.

EXAMPLE 27

3-Carboxy-7-nitrothioxanthone-10,10-dioxide

A. 7-Nitrothioxanthone-3-carboxylic acid

Sodium 4-nitrothiophenoxide (from 1.55g of 4-nitrothiophenol) was heated with 2,5-dicyanonitrobenzene (1.73g) in dimethylsulphoxide (30 ml) at 100° C. for 1 hr. After standing overnight the solution was diluted with water and dilute sodium carbonate and the precipitate of 2,5-dicyano-4'-nitrodiphenylsulphide (2.65g) collected by filtration. This compound had m.p. 181° C. when recrystallised. To hydrolyse the dinitrile, it was refluxed with a mixture of 60% w/w sulphuric acid (70 ml) and glacial acetic acid (45 ml) for 3.5 hr. and the resulting p-nitrothiophenoxyterephthalic acid filtered off. This was cyclised by heating with an excess of phosphorus oxychloride for 24 hr., removing the solvent under reduced pressure, and again heating for 21 hr. at 135° C. with an excess of polyphosphoric acid. On addition to warm water 2-nitrothioxanthone-6-carboxylic acid was precipitated; from a mixture of dimethylformamide, dimethylsulphoxide and ethanol, the acid formed crystals which sublimed but did not melt up to 410° C.

B. 3-Carboxy-7-nitrothioxanthone-10,10-dioxide

7-Nitrothioxanthone-3-carboxylic acid (0.65g), acetic acid (125 ml) and 30% hydrogen peroxide (3.0 ml) were boiled together under reflux for 18 hr. The solution was filtered off and 3-carboxy-7-nitrothioxanthone-10,10-dioxide crystallised out slowly and was filtered off and dried at 156° C. in vacuo, m.p. >360° C.

Found: C, 50.49%; H, 2.30%; N, 4.05%. $C_{14}H_7NO_7S$ requires C, 50.46%; H, 2.12%; N, 4.20%.

EXAMPLE 28

2,5-Dicarboxythioxanthone-10,10-dioxide

A. Thioxanthone-2,5-dicarboxylic acid

Sodium 4-cyanothiophenoxide (from 2.7g of 4-cyanothiophenol) was heated with 2,6-dicyanonitrobenzene (3.5g) in dimethylsulphoxide (20 ml at 110° C. overnight. On dilution with water, 2,4',6-tricyanodiphenylsulphide, m.p. 172°-173° C., was obtained. This was hydrolysed by refluxing for 5 hr. in 60% sulphuric acid (40 ml) and glacial acetic acid (25 ml); a solid precipitate of diphenylsulphide-2,4',6'-tricarboxylic acid being formed. This was cyclised in concentrated sulphuric acid at 90°-100° C: after 4 hr. heating the solution was poured onto ice. The resulting thioxanthone-2,5-dicarboxylic acid, on crystallisation from dimethylformamide-ethanol, formed crystals, m.p. ca. 400° C., which contained one quarter of a molecule of dimethyl formamide of solvation.

B. 2,5-Dicarboxythioxanthone-10,10-dioxide

Thioxanthone-2,5-dicarboxylic acid (0.52g), acetic acid (25 ml) and 30% hydrogen peroxide (1.5 ml) were boiled together under reflux for 2.5 hr. Further acetic acid (ca. 100 ml) was added to dissolve all of the product, the solution was filtered while boiling, and on cooling 2,5-dicarboxythioxanthone-10,10-dioxide crystallised out and was filtered off and dried, m.p. 350°-351° C.

Found: C, 53.94%; H, 2.46%;. $C_{15}H_8O_7S$ requires C, 54.22%; H, 2.43%.

EXAMPLE 29

1-Carboxythioxanthone-10,10-dioxide

A. Thioxanthone-1-carboxylic acid

Sodium thiophenoxide (from 3.3g of thiophenol) was heated at 100° C. in dimethylsulphoxide (30 ml) with 2,3-dicyanonitrobenzene (5.2g) for 4.5 hr. On dilution with water, 3-thiophenoxyphthalodinitrile, m.p. 116°-117° C., was obtained. This was refluxed with 60% sulphuric acid (105 ml) and acetic acid (66 ml) for 5.5 hr. to give the corresponding phthalic acid, which was then cyclized by heating with an excess of polyphosphoric acid for 72 hr. at 135°-145° C. Addition to warm water gave a precipitate of thioxanthone-1-carboxylic acid which yielded crystals, m.p. 264°-265° C. from a mixture of dimethyl formamide and aqueous ethanol.

B. 1-Carboxylthioxanthone-10,10-dioxide

Thioxanthone-1-carboxylic acid (0.60g), acetic acid (15 ml) and 30% hydrogen peroxide solution (0.60 ml) were boiled under reflux together for 8 hr., during which time a further two (0.60 ml) portions of peroxide were added at intervals. The boiling solution was filtered, and on cooling 1-carboxythioxanthone-10,10-dioxide crystallised out and was filtered off and dried, m.p. 269°-271° C.

Found: C, 58.08%; H, 2.84%. $C_{14}H_8O_5S$ requires C, 58.33%; H, 2.80%.

EXAMPLE A

Compression Coated Tablet

Example A

| Compression Coated Tablet | | |
|---|---|---|
| Core | 3-(5-Tetrazolyl)thioxanthone-10,10-dioxide sodium salt | 100 mg |
|  | Starch B.P. | 25 mg |
|  | Magnesium Stearate B.P. | 2 mg |
| Coating | Lactose B.P. | 320 mg |
|  | Starch B.P. | 50 mg |
|  | Gelatin B.P. | 6 mg |
|  | Magnesium Stearate B.P. | 4 mg |

Sodium Tetrazolyl salt and starch were granulated with water and dried. Magnesium stearate was added to the dried granule. Lactose and starch were granulated with a 10% w/v aqueous solution of gelatin and dried. Magnesium stearate was added to the dried granule. The granulated core was compressed with the granulated coating in a conventional compression moulding machine.

EXAMPLE B

Capsule

Example B

| Capsule | |
|---|---|
| 3-(5-Tetrazolyl)thioxanthone-10,10-dioxide sodium salt | 200 mg |
| Lactose B.P. | 200 mg |
| Talc B.P. | 40 mg |

Sodium tetrazolyl salt, lactose and talc were brought into intimate admixture with one another and 440 mg of the resultant mixture was introduced into a size 0 hard gelatin capsule.

Example C

| Lotion for Topical Use | |
|---|---|
| 3-(5-Tetrazolyl)thioxanthone-10, 10-dioxide sodium salt. | 1.5 g |
| Sorbitan Monolaurate | 0.6 g |
| Polysorbate 20 | 0.6 g |
| Cetostearyl Alcohol | 1.2 g |
| Glycerin | 6.0 g |
| Methyl Hydroxybenzoate | 0.2 g |
| Purified Water B.P. to | 100.0 ml |

The Methyl Hydroxybenzoate and Glycerin were dissolved in 70 ml. of the Water at 75° C. The Sorbitan Monolaurate, Polysorbate 20 and Cetostearyl Alcohol were melted together at 75° C and added to the aqueous solution. The resulting emulsion was homogenised, allowed to cool with continuous stirring and the Sodium Tetrazolyl salt added as a solution in the remaining Water. The whole was stirred until homogeneous.

Example D

| Inhalation Aerosol | |
|---|---|
| 3-Carboxythioxanthone-10,10-dioxide (0.5 – 7.0 μm powder) | 200 mg |
| Sorbitan Trioleate | 100 mg |
| Saccharin Sodium (0.5 – 7.0 μm powder) | 5 mg |
| Menthol | 2 mg |
| Trichlorofluoromethane | 4.5 g |
| Dichlorodifluoromethane to | 10.0 ml |

The Sorbitan Trioleate and Menthol were dissolved in the Trichlorofluoromethane. The Saccharin Sodium and Carboxylic Acid were dispersed in the mixture which was then transferred to a suitable aerosol canister and the Dichlorodifluoromethane injected through the valve system. This composition provides 10 mg. of Acid in each 100 ml. dose.

Example E

| Lozenge | |
|---|---|
| 3-(5-Tetrazolyl)thioxanthone-10,10-dioxide sodium salt. | 50 mg |
| Mannitol | 400 mg |
| Dextrose Monohydrate | 400 mg |
| Magnesium Stearate | 20 mg |

The Sodium Tetrazolyl salt was mixed with the Dextrose Monohydrate and Mannitol; granulated with the ethanolic Polyvinylpyrrolidone solution and then dried. The Magnesium Stearate was sifted on and the resulting mixture compressed to produce lozenges of the desired shape.

Example F

| Capsule | |
|---|---|
| 3-(5-Tetrazolyl)thioxanthone-10,10-dioxide | 100 mg |
| Lactose | 100 mg |
| Maize Starch | 100 mg |
| Magnesium Stearate | 10 mg |

The ingredients were mixed together until homogeneous and 310 mg of the resulting mixture filled into each hard gelatin capsule.

Example G

| Tablet | |
|---|---|
| 3-Carboxythioxanthone-10,10-dioxide | 500 mg |
| Maize Starch | 100 mg |
| Microcrystalline Cellulose | 75 mg |
| Magnesium Stearate | 10 mg |

The Carboxylic Acid, Maize Starch and Microcrystalline Cellulose were mixed together, and granulated with the alcoholic Polyvinylpyrrolidone. The resulting granules were dried, and compressed to produce tablets, each tablet having a weight of approximately 690 mg.

Example H

| Foaming Non-aqueous Aerosol for Topical Use | |
|---|---|
| 3-Carboxythioxanthone-10,10-dioxide (fine powder) | 5.0 g |
| Polyethylene Glycol 400 | 80.0 g |
| Propylene Glycol Monostearate, self-emulsifying | 5.0 g |
| Dichlorodifluoromethane (Propellant 12) | 4.0 g |
| Dichlorotetrafluoroethane (Propellant 114) | 6.0 g |

The Carboxylic acid was dispersed in a mixture of the Propylene Glycol Monostearate, self-emulsifying, and the Propylene Glycol. An aerosol canister, was filled with the mixture, the valve sealed on and pressurisation effected by injecting the propellants through the valve.

Example I

| Foaming Aqueous Aerosol for Topical Use | | |
|---|---|---|
| Part A | 3-Carboxythioxanthone-10,10-dioxide sodium salt | 2.2 g |
| | Triethanolamine | 3.2 g |
| | Glycerin | 4.7 g |
| | Polyvinylpyrrolidone | 0.3 g |
| | Purified Water B.P. | 81.0 g |
| Part B | Myristic Acid | 1.3 g |
| | Stearic Acid | 5.3 g |
| | Cetyl Alcohol | 0.5 g |
| | Lanolin | 0.2 g |
| | Isopropyl Myristate | 1.3 g |
| Propellents | Dichlorodifluoremethane | 4.0 g |
| | Dichlorotetrafluoroethane | 6.0 g |

The ingredients of Part B were melted together at 70° C. A solution of the ingredients of Part A in the Purified Water at the same temperature, was added to the melted ingredients of Part B. The resulting emulsion was homogenised and cooled to room temperature. The emulsion was filled into an aerosol canister, the valve crimped on and pressurisation effected by injecting the mixed propellents through the valve.

Example J

| Spray on Film for Topical Use | | |
|---|---|---|
| 3-(5-Tetrazolyl)thioxanthone-10,10-dioxide (fine powder) | 5.0 | g |
| Polyethylene Glycol 600 | 0.8 | g |
| Menthol | 0.01 | g |
| Acetone | 43.5 | g |
| Ethyl Alcohol Absolute | 45.69 | g |
| Polyvinylpyrrolidone/Vinyl Acetate Copolymer (40:60) (PVP/VA) | 5.0 | g |
| Dichlorodifluoromethane (Propellant 12) | 30.0 | g |
| Dichlorotetrafluoroethane (Propellant 114) | 70.0 | g |

The Polyethylene Glycol 600, Menthol and PVP/VA Copolymer were dissolved in a mixture of the Acetone and Ethyl Alcohol. The Carboxylic Acid was added and dispersed. The mixture was transferred to a suitable aerosol canister, the valve crimped on and pressurisation effected by injecting the mixture of propellants through the valve.

Example K

| Nasal Drops | |
|---|---|
| 3-Carboxythioxanthone-10,10-dioxide sodium salt | 5.0 g |
| Chlorbutol | 0.5 g |
| Purfied Water B.P. to | 100.0 ml |

The ingredients were dissolved in 95 ml. Purified water at room temperature. The resulting mixture was made up to 100mls with Purified Water and clarified by filtration.

Example L

| Eye Drops | |
|---|---|
| 3-Carboxythioxanthone-10,10-dioxide sodium salt | 5.0 g |
| Methyl Hydroxybenzoate | 0.10 g |
| Propyl Hydroxybenzoate | 0.04 g |
| Purified Water B.P. to | 100.00 ml |

The Methyl and Propyl Hydroxybenzoates were dissolved in 70 ml. Purified Water at 75° C and the resulting solution then allowed to cool. The sodium carboxylate salt was added next and the solution made up to 100 ml. with purified water. The solution was sterilised by filtration through a membrane filter 0.22μm pore size and packed aseptically into suitable sterile containers.

Example M

| Powder Capsules for Inhalation | |
|---|---|
| 3-(5-Tetrazolyl)thioxanthone-10,10-dioxide sodium salt (0.5-7.0 μm powder) | 4.0 mg |
| Lactose (30-90 μm powder) | 46.0 mg |

The powders were mixed until homogeneous and filled into suitably sized hard gelatin capsules, 50 mg of mixture per capsule.

Example N

| Injection Solution | |
|---|---|
| 3-Carboxythioxanthone-10,10-dioxide sodium salt | 50.0 mg |
| Water for Injections B.P. to | 1.0 ml |

The sodium carboxylate salt was dissolved in half of the Water and then made up to volume and sterilised by filtration. The resulting solution was distributed into ampoules under aseptic conditions.

Example O

| Suppositories | |
|---|---|
| 3-Carboxythioxanthone-10,10-dioxide | 200 mg |
| Suppository Base | 1.8 g |

The carboxylic acid in fine powder form was dispersed into a little of the molten Suppository Base at 50° C. The dispersion was incorporated into the bulk of the base at the same temperature, allowed to cool at 42°–45° C. and poured into suitable 2g suppository moulds and allowed to set at 15°–20° C. Suppository Bases were Massa Esterinum C and Witten H Suppository Compound.

Example P

| Dispersible Tablet | Per tablet |
|---|---|
| 3-carboxythioxanthone-10,10-dioxide | 200.00 mg |
| Maize Starch | 40.00 mg |
| Primojel (Trade name: sodium starch glycollate (125 μm powder) | 50.00 mg |
| Dicalcium Phosphate Dihydrate | 50.00 mg |
| Sodium Carboxymethyl Cellulose | 2.00 mg |
| Dioctyl Sodium Sulphosuccinate | 0.25 mg |
| Sodium Saccharin | 5.00 mg |
| Microcrystalline Cellulose | 50.00 mg |
| Magnesium Stearate | 3.00 |
| | 400.25 mg |

The carboxylic acid, half of the Maize Starch, the Primejel and Dicalcium Phosphate were mixed together and then granulated with a solution of Sodium Carboxymethyl Cellulose, Dioctyl Sodium Sulphosuccinate and Sodium Saccharin in a suitable volume of 50% Ethyl Alcohol. The granules were dried, the remaining Maize Starch, the Microcrystalline Cellulose and the Magnesium Stearate were blended in and the resulting mixture compressed into tablets each having a weight of 400.25 mg.

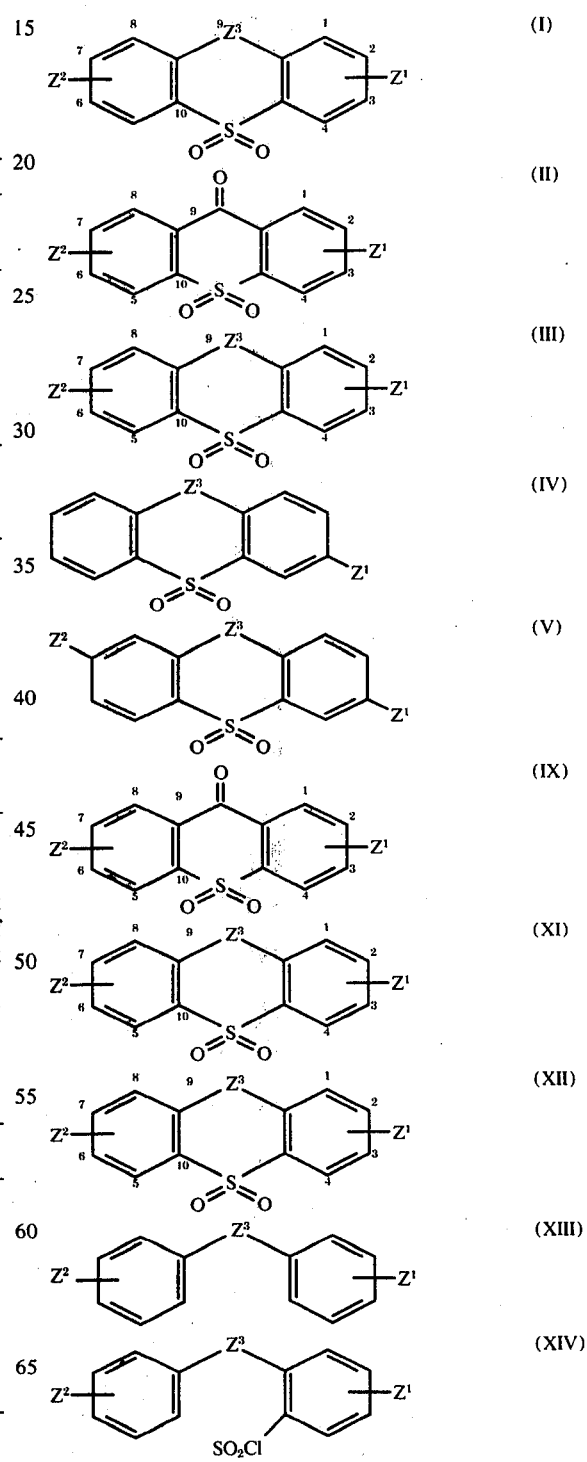

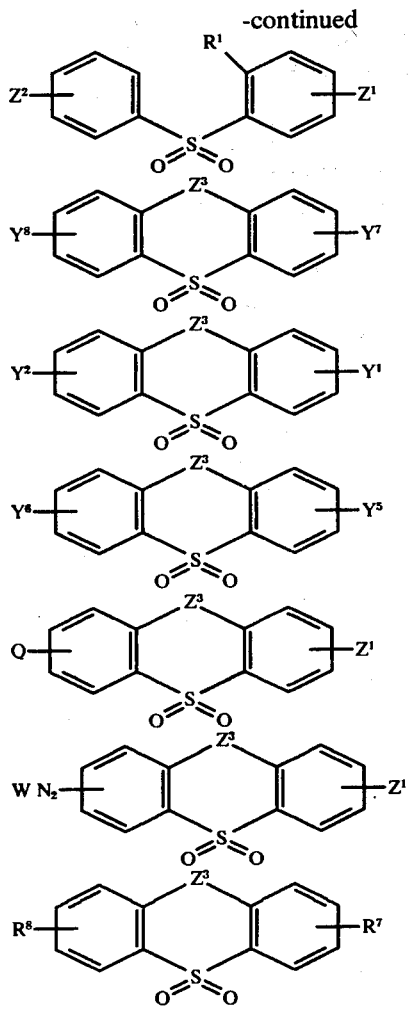

What we claim is:

1. A method for the treatment or prophylaxis of an allergic condition of a mammal comprising administration to the mammal of a therapeutically or prophylactically effective anti-allergic dose of a tricyclic compound selected from 3-(5-tetrazolyl) thioxanthone-10,10-dioxide, and pharmaceutically acceptable salt of said compound.

2. The method of claim 1 wherein said tricyclic compound or salt thereof is administered by the oral route.

3. A method as claimed in claim 2 wherein said tricyclic compound or salt thereof is administered at a dose of 1 to 50 mg. per kilogram body weight of said mammal.

4. A method as claimed in claim 3 wherein said allergic condition is allergic asthma.

5. A method as claimed in claim 3 wherein said allergic condition is hay fever.

6. A method for the treatment or prophylaxis of allergic asthma of a mammal comprising administration of said mammal of a dose of 1 to 50 mg. per kilogram body weight of said mammal of 3-(5-tetrazolyl)thioxanthone-10,10-dioxide.

7. A method as claimed in claim 1 wherein said salt is a sodium salt.

8. A method as claimed in claim 1 wherein said tricyclic compound or salt thereof is administered by the pulmonary route.

9. A method as claimed in claim 8 wherein the tricyclic compound is administered as a powder having a particle size in the range of 0.5 to 7$\mu$.

10. The method of claim 9 wherein the tricyclic compound is administered at a dose of 5$\mu$g. of 0.5 mg. per kilogram body weight of said mammal.

11. A pharmaceutical composition comprising an effective anti-allergic, non-toxic amount of a tricyclic compound selected from 3-(5-tetrazoyl)thioxanthone-10,10-dioxide, and pharmaceutically acceptable salt thereof; said compound in association with a pharmaceutically acceptable carrier therefor.

12. A composition as claimed in claim 11 wherein the composition is in a form adapted for oral administration.

13. A composition as claimed in claim 12 wherein the composition is in the form of discrete dosage units, each containing an effective anti-allergic, non-toxic amount of said tricyclic compound.

14. A composition as claimed in claim 13 wherein the composition is in the form of a tablet, capsule, lozenge or sachet.

15. A composition as claimed in claim 13 wherein the composition is in the form of a coated, moisture resistant tablet.

16. A composition as claimed in claim 13 wherein each discrete unit contains from 50 to 500 mg. of said tricyclic compound.

17. A pharmaceutical composition as claimed in claim 11 wherein said tricyclic compound is in the form of a powder adapted for pulmonary administration.

18. A composition as claimed in claim 17 wherein said powder has a particle size in the range of 0.5 to 7$\mu$.

19. A composition as claimed in claim 17 wherein the composition comprises a self-propelling aerosol composition in a sealed valved container in which said tricyclic compound is dispersed in a liquid propellant.

20. A pharmaceutical composition as claimed in claim 17 wherein said powdered tricyclic compound is incorporated in a capsule suitable for use in an inhalation device.

21. A pharmaceutical composition in the form of a tablet comprising an effective antiallergic, non-toxic amount of 3-(5-tetrazolyl)thioxanthone-10,10-dioxide or a pharmaceutically acceptable salt thereof, in association with a pharmaceutically acceptable carrier therefor.

22. A pharmaceutical composition as claimed in claim 21 wherein the tablet comprises from 50 to 500mg of the tricyclic compound.

23. A pharmaceutical composition in the form of a capsule containing an effective antiallergic, non-toxic amount of a tricyclic compound selected from 3-(5-tetrazolyl)thioxanthone-10,10and pharmaceutically acceptable salt thereof.

24. A method for the treatment or prophylaxis of asthma in a mammal comprising the administration to the mammal of an effective, non-toxic amount of 3-(5-tetrazolyl)thioxanthone-10,10-dioxide or a pharmaceutically acceptable salt thereof.

25. A method for the treatment or prophylaxis of allergic rhinitis in a mammal comprising the administration to the mammal of an effective, non-toxic amount of 3-(5-tetrazolyl)thioxanthone10,10-dioxide or a pharmaceutically acceptable salt thereof.

26. A pharmaceutical composition comprising an effective anti-asthmatic, non-toxic amount of a tricyclic compound selected from 3-(5-tetrazolyl)thioxanthone-10,10-dioxide and pharmaceutically acceptable salt thereof; said compound in association with a pharmaceutically acceptable carrier therefor.

27. A pharmaceutical composition comprising an effective anti-allergic rhinitis, non-toxic amount of a tricyclic compound selected from 3-(5-tetrazolyl)thioxanthone-10,10-dioxide and pharmaceutically acceptable salt thereof; said compound in association with a pharmaceutically acceptable carrier therefor.

* * * * *